United States Patent
Bort et al.

(10) Patent No.: US 12,414,991 B2
(45) Date of Patent: Sep. 16, 2025

(54) AZOBENZENE DERIVATIVES, PROCESS FOR THEIR PREPARATION AND THEIR USE FOR THERAPEUTIC TREATMENT ASSOCIATED WITH IONIZING RADIATIONS

(71) Applicants: CENTRE NATIONAL DE LA RECHERCHE SCIENTIFIQUE, Paris (FR); UNIVERSITE PARIS-SACLAY, Gif sur Yvette (FR); INSTITUT CURIE, Paris (FR)

(72) Inventors: Guillaume Bort, Paris (FR); Patrick Couvreur, Paris (FR); Simona Mura, Paris (FR); Frédéric Pouzoulet, Breuillet (FR)

(73) Assignees: CENTRE NATIONAL DE LA RECHERCHE SCIENTIFIQUE, Paris (FR); UNIVERSITE PARIS-SACLAY—RAISON SOCIALE OBSOLETE, Saint-Aubin (FR); INSTITUT CURIE, Paris (FR)

( * ) Notice: Subject to any disclaimer, the term of this patent is extended or adjusted under 35 U.S.C. 154(b) by 1066 days.

(21) Appl. No.: 17/428,406

(22) PCT Filed: Feb. 7, 2020

(86) PCT No.: PCT/EP2020/053144
§ 371 (c)(1),
(2) Date: Aug. 4, 2021

(87) PCT Pub. No.: WO2020/161308
PCT Pub. Date: Aug. 13, 2020

(65) Prior Publication Data
US 2022/0125923 A1   Apr. 28, 2022

(30) Foreign Application Priority Data
Feb. 8, 2019  (FR) .................................... 1901285

(51) Int. Cl.
| A61P 35/00 | (2006.01) |
|---|---|
| A61K 31/555 | (2006.01) |
| A61K 39/395 | (2006.01) |
| A61K 41/00 | (2020.01) |
| C07D 257/02 | (2006.01) |

(52) U.S. Cl.
CPC ........ *A61K 41/0085* (2013.01); *A61K 31/555* (2013.01); *A61K 39/3955* (2013.01); *A61P 35/00* (2018.01); *C07D 257/02* (2013.01)

(58) Field of Classification Search
CPC .... A61K 41/0085; A61P 35/00; C07D 257/02
See application file for complete search history.

(56) References Cited

U.S. PATENT DOCUMENTS

| 2003/0206865 A1 | 11/2003 | Platzek et al. |
| 2010/0322855 A1* | 12/2010 | Chong .................. C07J 43/003 514/183 |

FOREIGN PATENT DOCUMENTS

| CN | 1541114 A | 10/2004 | |
| CN | 104447598 A | * 3/2015 | ........... C07D 255/02 |
| JP | 62281310 A | 12/1987 | |
| WO | 2011168189 A1 | 12/2011 | |
| WO | 2018051197 A1 | 3/2018 | |

OTHER PUBLICATIONS

Griffith et al. The Synergy Between Ionizing Radiation and Immunotherapy in the Treatment of Prostate Cancer. Immunotherapy vol. 9, Oct. 2017, pp. 1005-1018. (Year: 2017).*
CN104447598 A Machine Translation (Year: 2015).*
Bort et al. Gadolinium-based contrast agents targeted to amyloid aggregates for the early diagnosis of Alzheimer's disease by MRI, Euro Journal of Med., Nov. 2014, pp. 843-861 (Year: 2014).*
Bort, G. et al., "Gadolinium-based contrast agents targeted to amyloid aggregates for the early diagnosis of Alzheimer's disease by MRI", European Journal of Medicinal Chemistry 87, 2014.
Berge, S. et al., "Pharmaceutical Salts", Journal of Pharmaceutical Sciences 66 No. 1, 1977.
Frullano, L. et al., "Synthesis and Characterization of a Novel Gadolinium-Based Contrast Agent for Magnetic Resonance Imaging of Myelination", Journal of Medicinal Chemistry 56, 2013.
ACS Registry Entered Nov. 27, 2014.
Ren and Chloe Z.-J. et al Reversible formation of a light-responsivecatalyst byutilizing intermolecular cooperative effects, Angewandte Chemie, InternationalEditio n-2019 years, 58 (43), 15254-15258.

* cited by examiner

*Primary Examiner* — Sarah Pihonak
*Assistant Examiner* — Mikhail O'Donnel Robinson
(74) *Attorney, Agent, or Firm* — WCF IP

(57) ABSTRACT

The present invention relates to new ionizing radiation-activatable derivatives, their preparation process and their therapeutic uses.

12 Claims, 2 Drawing Sheets

Figure 1:
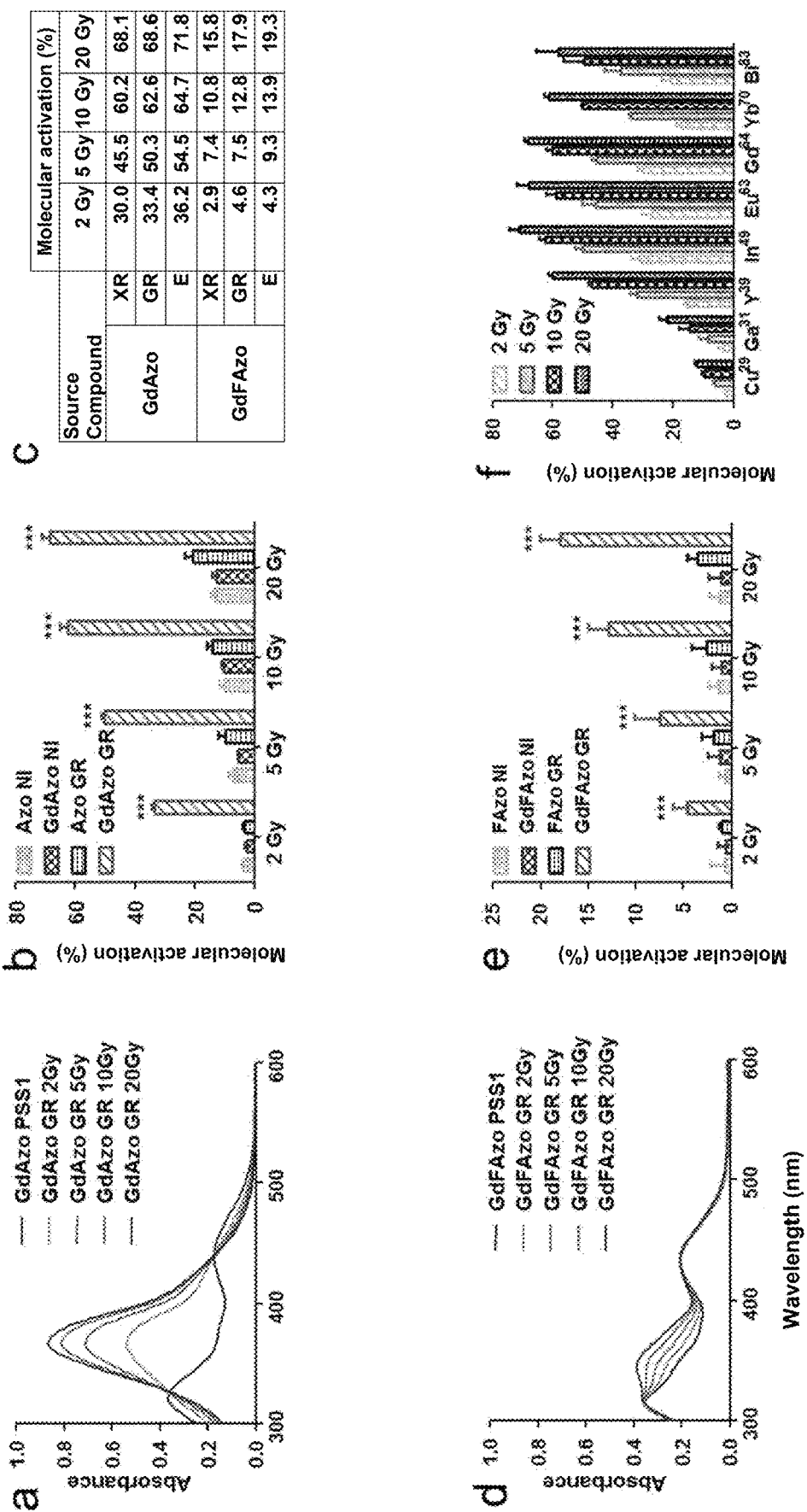

AZOBENZENE DERIVATIVES, PROCESS FOR THEIR PREPARATION AND THEIR USE FOR THERAPEUTIC TREATMENT ASSOCIATED WITH IONIZING RADIATIONS

The present invention relates to the therapeutic treatment of pathologies such as cancer, by means of compounds activatable by ionizing radiation.

Redox and light-sensitive systems have been developed for more than a century and are used to trigger complex actions, such as specific bond cleavage or configuration switching, which can be used to effect the release of active molecules, control protein activity and gene expression, etc. Unfortunately, clinical applications of these sensitive systems are still limited to topical or ophthalmic treatment, due to the current paucity of techniques capable of activating these systems at depths greater than a few hundred micrometres below the body surface, with the exception of the use of invasive electrodes or optical fibres. Indeed, all the photosensitive molecules developed so far are only sensitive to UV, visible or near infrared radiation, whose penetration into the tissues is intrinsically limited.

The activation of compounds triggered by ionizing radiation has been proposed in WO 2011/158189. However, efficacy is extremely limited, and requires doses that are too high to be applied clinically.

It is therefore desirable to make available new compounds that can be activated by irradiation without restricting depth in the targeted biological tissues. Ionizing radiation can be used to effectively reach deep tissue, where the high energy of the radiation will be converted locally to specifically activate redox/photosensitive therapeutic systems.

According to the invention, a molecular energy converter (metal chelate) is combined with a photosensitive switch (an azobenzene moiety) to give a photosensitive system that can be activated by highly penetrating light at moderate doses compatible with clinical applications.

According to a first object, the present invention therefore relates to a compound of formula (I):

[Chem 1]

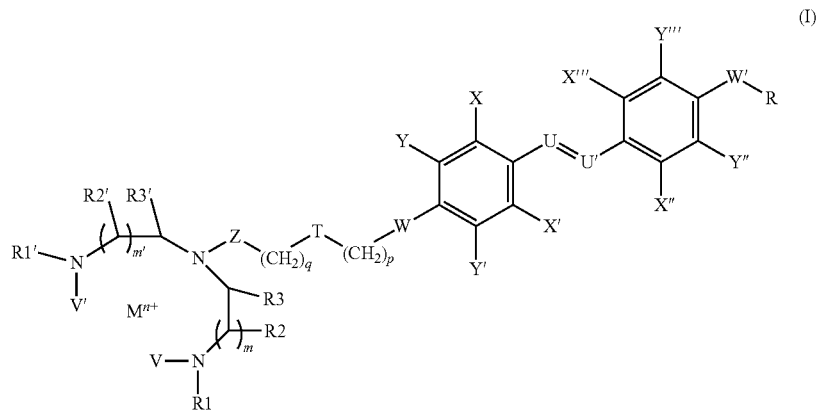

(I)

In which:
M represents a metal atom selected from Ce(III), Pr(III), Nd(III), Sm(III), Eu(III), Gd(III), Tb(III), Dy(III), Ho(III), Er(III), Tm(III), Yb(III), Mg(II), Ca(II), Mn(II), Fe(II), Fe(III), Cu(II), Zn(II), Ga(III), Y(III), Zr(III), Tc(IV), Tc(VI), Tc(VII), Ru(II), Ru(III), Ru(IV), Pd(II), Ag(I), In(III), Hf(IV), Re(VI), W(II), W(III), W(IV), W(V), W(VI), Os(III), Os(IV), Ir(III), Ir(IV), Pt(II), Au(I), Au(III), Tl(III), Zr(IV), Nb(III), Bi(III);

n is 1, 2, 3, 4, 5, 6, or 7;

V and V', which may be identical or different, are hydrogen atoms or linear or branched C1-C10 alkyl or alkoxy chains, or C1-C10 alkyl chains linked together and comprising one or more heteroatoms selected from N, O, or S, optionally substituted with one or more substituents independently selected from halogen atoms, and nitrile, nitro, thio, amino, amido, aryl, heteroaryl, hydroxyl, carboxylic acid or carboxylate groups, to form a ring;

R1, R1', R2, R2', which may be identical or different, are hydrogen atoms, or linear or branched C1-C10 alkyl or alkoxy chains optionally substituted with one or more substituents independently selected from halogen atoms, and nitrile, nitro, thio, amino, amido, aryl, heteroaryl, hydroxyl, carboxylic acid or carboxylate groups;

R3 and R3', which may be identical or different, are hydrogen atoms or linear or branched C1-C10 alkyl or alkoxy chains optionally substituted with one or more substituents independently selected from halogen atoms, and nitrile, nitro, thio, amino, amido, aryl, heteroaryl, hydroxyl, carboxylic acid or carboxylate groups, or R3 and R3' are linked together to form a 5- to 14-membered heterocycle or heteroaryl;

m and m', which may be identical or different, are equal to 1 or 2;

X, X', X'', X''', Y, Y', Y'', Y''', which may be identical or different, are independently selected from H; halogen atoms; alkoxy, alkyl or cycloalkyl groups optionally interrupted or substituted with one or more heteroatom(s) or group(s) COOH, CONH$_2$, COSH, OH, NH$_2$, SH; 5- to 12-membered aryl or heteroaryl groups optionally substituted with one or more COOH, CONH$_2$, COSH groups; COOH or NH$_2$ groups;

Z represents an alkyl group optionally interrupted or substituted with one or more heteroatom(s) or a COOH, CONH$_2$, COSH, OH, NH$_2$, SH group; a 5- to 12-membered aryl or heteroaryl group optionally substituted with one or more COOH, CONH$_2$, COSH groups; or a COOH or NH$_2$ group;

W and W', which may be the same or different, independently represent a $CH_2$ group; or an aryl or cycloalkyl group; an oxygen or nitrogen atom (secondary or ternary); an amide linkage; an ester linkage; a thioether linkage;

U and U', which may be the same or different, represent the CH or NH group, it being understood that the double bond U=U' is in cis or trans form;

T represents a $CH_2$ group; a —C(=O)NH group; an alkoxy, alkyl or cycloalkyl group optionally interrupted or substituted with one or more heteroatom(s) or a COOH, $CON_2$, COSH, OH, $NH_2$, SH group; a 5- to 12-membered aryl or heteroaryl group containing one or more heteroatom(s) and/or optionally substituted with one or more groups chosen from COOalkyl, CONHalkyl, COSHalkyl;

R represents H, or linear or branched C1-C18 alkyl or alkoxy chain, optionally substituted with one or more substituents independently selected from halogen atoms, and nitrile, nitro, thio, amino, amido, aryl, heteroaryl, hydroxyl, carboxylic acid or carboxylate groups;

p and q are integers between 0 and 6, in particular between 1 and 6;

It being understood that in order to ensure the neutrality of the molecule, the n cationic charges of M can be neutralized by 0 to n carboxylate groups (—COOH) optionally substituted on R1, R1', R2, R2', R3, R3', V, V, and/or by 0 to n of the counterions present in solution if necessary;

In the form of cis and/or trans isomers and mixtures thereof

Or a pharmaceutically acceptable salt thereof.

The compounds according to the invention are able to induce the permeability and death of cancer cells when activated by ionizing radiation. After introduction of the inactive (cis) form, irradiation of the target site with ionizing radiation is applied. This radiation induces a conversion of the molecule into its active form (trans) leading to cell permeability and death due to the change in the lipophilic balance of the molecule. The rays used to activate the molecule penetrate biological tissues without depth restriction, making the activation technique perfectly suited for clinical applications, unlike traditional photosensitive tools whose activation is limited to UV to near-infrared irradiation (penetration of less than 1 cm of biological tissue).

The compounds according to the inventions are radio-sensitive in that their action is triggered by ionizing radiation. They therefore represent a promising tool for the control and modulation of therapeutic actions in real time.

Metal atoms with sizes between Z=20 and Z=83, and in particular the following metals Fe, Cu, Zn, Ga, Y, Zr, Tc, Ru, Pd, Ag, In, Eu, Gd, Tb, Dy, Ho, Yb, Hf, W, Os, Ir, Pt, Au, Bi.

In the aforementioned general formula (I), the following embodiments are envisaged, separately or in any combination thereof:

V and V are linked together by means of a C1-C9 alkyl chain, comprising 2 nitrogen atoms, optionally substituted with 2 carboxylate groups; and/or V and V' are linked to form the chain:

[Chem 2]

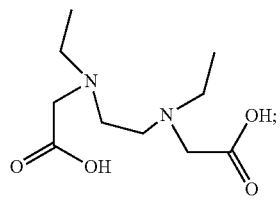

and/or

Z represents a —CH(COOH)— group; and/or m=m'=1; and/or

R2=R3=R2'=R3'=H; and/or R1=R1'=(CH2)COOH; and/or p=q=2; and/or

Y=Y'=Y"=Y'"=H;

W=W'=O;

U=U'=NH.

According to one embodiment, the compounds of formula (I) have the general formula (IA):

[Chem 3]

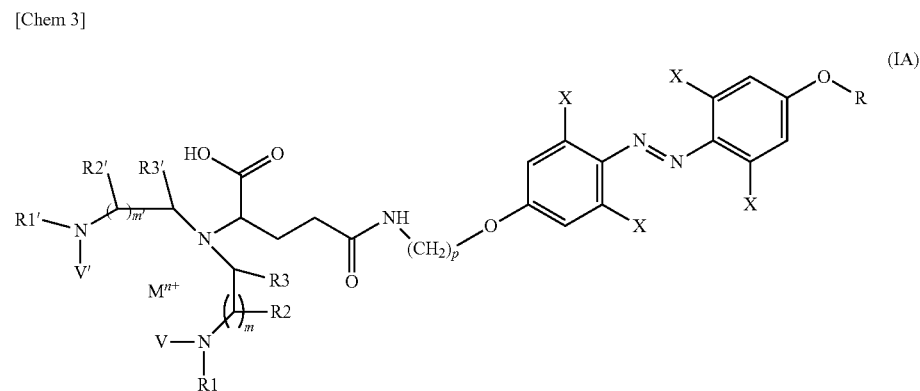

(IA)

In which:
M, n, R1, R2, R3, V, m, R1', R2', R3', V, m', p are defined as in formula (I) and
X is selected from hydrogen and halogen atoms;
R is a linear or branched C1-C12 alkyl group;
The N=N double bond is in cis or trans form;
It being understood that in order to ensure the neutrality of the molecule, the n cationic charges of M can be neutralized by 0 to n carboxylate groups (—COOH)

substituted on R1, R1', R2, R2', R3, R3', V, V, and/or by 0 to n of the counterions present in solution if necessary;

Or a pharmaceutically acceptable salt.

According to one embodiment, the compounds of formula (I) have the general formula (IB):

[Chem 4]

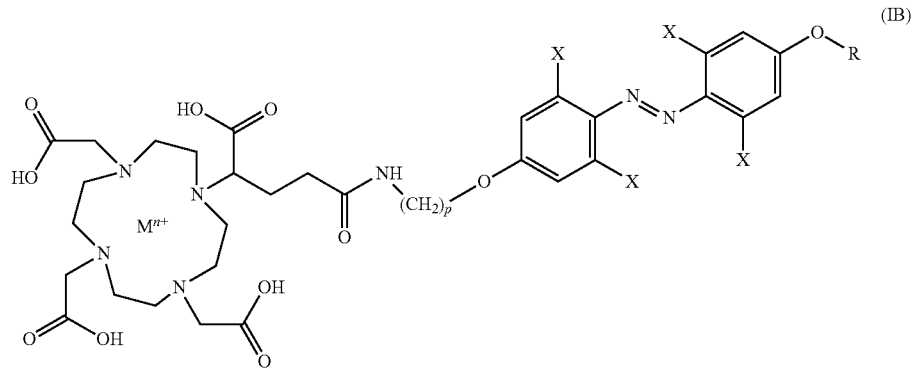

in which

M, n, p, X and R are defined as above, or a pharmaceutically acceptable salt.

According to one embodiment, the compounds of formula (I) have the general formula (IC):

[Chem 5]

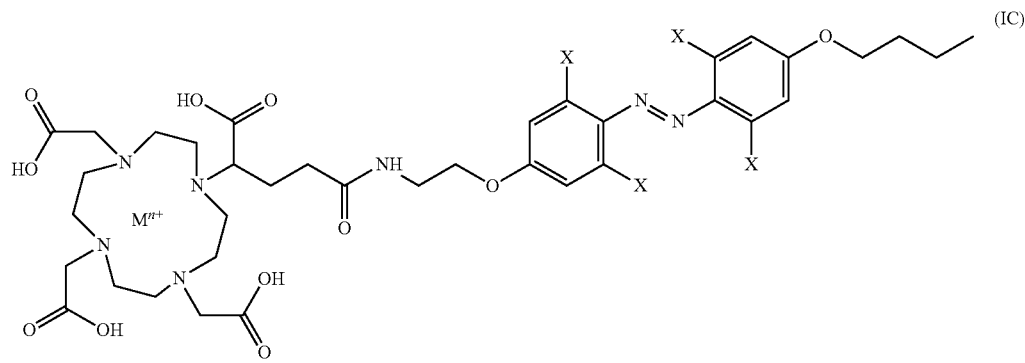

in which

M, n, X are defined as above, or a pharmaceutically acceptable salt.

According to one embodiment, in formula (I), (IA) or (IB):

X is selected from H and F; and/or

R represents a linear C4-C8 alkyl group;

p=2;

M is a metal selected from Cu, Ga, Y, In, Eu, Gd, Yb, Bi;

n=2 or 3.

In the above and the following:

"Alkyl" means an aliphatic hydrocarbon group which may be linear or branched having about 1 to about 20 carbon atoms in the chain. Preferred alkyl groups have 1 to about 12 carbon atoms in the chain. Branched means that one or more lower alkyl groups, such as methyl, ethyl or propyl, are linked to a linear alkyl chain.

"Alkoxy" means an alkyl-O— group, wherein the alkyl group is as described above. Typical examples of alkoxy groups include methoxy, ethoxy, n-propoxy, i-propoxy, n-butoxy and heptoxy.

"Cycloalkyl" means a non-aromatic mono- or multi-cyclic ring system of about 3 to about 10 carbon atoms, preferably of about 5 to about 10 carbon atoms. Preferred ring sizes of the ring system include about 5 to about 6 ring atoms. Example monocyclic cycloalkyls include cyclopentyl, cyclohexyl, and cycloheptyl.

"Carboxy" means an HO(O)C— group (carboxylic acid).

"Aryl" means an aromatic monocyclic or multicyclic ring system with about 6 to about 14 carbon atoms, preferably with about 6 to about 10 carbon atoms. Typical examples of aryl groups include phenyl and naphthyl.

"Heteroaryl" means an aromatic monocyclic or multicyclic ring system of about 5 to about 14 carbon atoms, preferably of about 5 to about 10 carbon atoms, wherein one or more of the carbon atoms in the ring system is/are a hetero element(s) other than carbon, e.g. nitrogen, oxygen or sulphur. Preferred ring sizes of the ring system include about 5 to about 6 ring atoms. Example heteroaryl groups include pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidinyl pyrrolopyridyl, imidazopyridyl, benzoazaindole, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl.

"Halogen" means fluorine, chlorine, bromine or iodine. Preferred are fluorine, chlorine or bromine, especially fluorine.

The present invention also relates to the therapeutic use of the compounds according to the invention.

According to another object, the present invention relates to pharmaceutical compositions comprising a compound of formula (I) predominantly in cis form, and at least one pharmaceutically acceptable excipient.

According to another object, the present invention relates to a compound of formula (I) in cis and/or trans form for use in the treatment of cancer.

The compounds of formula (I) below are activatable by ionizing irradiation, the cis double bond switching to the cytotoxic transform.

Said use therefore comprises administering a compound of formula (I) in a predominantly cis form and applying irradiation to the target site so as to form the trans form compound in situ.

Said use also includes monitoring of the treatment by in vivo MRI, PET, X-ray or SPECT imaging.

According to one embodiment, said use comprises administering an effective amount of a compound of formula (I), in cis form, to a patient in need thereof.

According to one embodiment, the administration of said compound of formula (I) may generally be carried out parenterally.

The ionizing radiation considered generally corresponds to the radiation used in radiotherapy treatments. Such actions induced by an external stimulus allow temporal and spatial control and can be adjusted on demand in real time to achieve optimal therapeutic efficacy. These include ionizing radiation such as photons (X-rays and γ-rays with energies ranging from 1 keV to 25 MeV), electrons and hadrons (such as protons or carbons with energies ranging from 60 to 300 MeV), and in particular X-rays (1-200 keV), gamma rays (662 keV) and electron beams (4500 keV).

This radiation allows the desired activation to be achieved at low doses of between 2 and 20 Gy, in particular between 2 and 10 Gy, more particularly between 2 and 5 Gy.

As the action of the compounds of the invention is exerted through cell permeability, all cancers can potentially be treated by the compounds of the invention, as the therapeutic approach is not limited to a specific cell surface signature. These include lung cancer, pancreatic cancer, liver cancer, spleen cancer, small cell lung carcinoma, prostate cancer, rhabdomyosarcoma, stomach cancer, gastrointestinal cancer, colorectal cancer, kidney cancer, breast cancer, ovarian cancer, testicular cancer, thyroid cancer, head and neck cancer, skin cancer, soft tissue sarcoma, bladder carcinoma, bone cancers, myeloma, plasmacytoma, germ cell cancer, uterine cancer, leukemia, lymphoma, neuroblastoma, osteosarcoma, retinoblastoma, central nervous system cancers, Wilms' tumors and especially pancreatic cancer or leukemia.

In one embodiment, the use also allows the presence of the compound and possibly its molecular switching to be detected in vivo by MRI due to the presence of metal atom(s) in the molecular structure of the compounds of the invention.

MRI detection of the compounds of the invention allows the localization and monitoring of the therapeutic action of said compounds in a non-invasive way, thus facilitating the development and monitoring of therapeutic protocols, and thus allowing a theranostic approach.

According to one embodiment, the compounds of the invention may be administered in combination with one or more anti-cancer agents, e.g. chemotherapy or immunotherapy such as immune checkpoint inhibitors like anti-CTLA4, anti-PD-L1 and anti-PD1.

"Effective amount" means an amount of a compound/composition according to the present invention effective at producing the desired therapeutic effect.

"Formulations suitable for parenteral administration" means formulations that are in a form suitable for parenteral administration to a patient. Formulations are sterile and include emulsions, suspensions, aqueous and non-aqueous injection solutions, which may contain suspending and thickening agents and anti-oxidants (after checking that the potentially radioprotective effect of these does not prevent the desired effect under radiation), buffers, bacteriostats and solutes that make the formulation isotonic, and have a pH adjusted appropriately, with the desired recipient blood.

The formulation is preferably administered by injection, including transmuscular, intravenous, intraperitoneal, and subcutaneous. For injection, the useful compounds according to the invention can be formulated in liquid solutions, preferably in physiologically compatible buffers such as Hank's solution or Ringer's solution. In addition, the compounds can be formulated in solid form and redissolved or suspended immediately before use. Freeze-dried forms are also included.

The choice of vehicle and the content of the active substance in the vehicle are generally determined by the solubility and chemical properties of the active compound, the particular mode of administration and the provisions to be observed in pharmaceutical practice.

The formulations may be prepared in individual pharmaceutical form by any of the methods well known in the art of pharmacy. These methods include the step of combining the active ingredient and the carrier which constitutes one or more accessory ingredients. In general, formulations are prepared by uniformly and intimately combining the active ingredient and liquid carriers or finely fractionated solid carriers or both and then, if necessary, shaping the product.

The actual dosage levels of an active ingredient in the compositions of the invention may vary in order to obtain an effective amount of active ingredient to achieve a desired therapeutic response for a particular composition and mode of administration. The dosage level chosen therefore depends on the desired therapeutic effect, the mode of administration, the desired duration of treatment, and other factors.

The dosage unit compositions may contain such quantities of such sub-multiples thereof as may be used to constitute the daily dose. It will be understood, however, that the specific dose level for any particular patient will depend on a variety of factors including body weight, general health, gender, diet, timing and method of administration, rates of absorption and excretion, combination with other drugs and the severity of the disease being treated.

The amount of each component administered is determined by the treating physicians taking into account the etiology and severity of the disease, the condition and age of the patient, the potency of each component and other factors.

Formulations can be presented in single- or multi-dose containers, e.g. ampoules and vials sealed with elastomeric closures, and can be stored in freeze-dried form requiring only the addition of a sterile liquid carrier, e.g. water for injections, just prior to use. Extemporaneously prepared solutions in injections and suspensions may be prepared from sterile powders, granules and tablets of the type described above.

"Liquid dose form" means that the dose of the active compound to be administered to the patient is in liquid form, for example, emulsions, solutions, suspensions, syrups and pharmaceutically acceptable elixirs. In addition to the active compounds, the liquid dosage forms may contain inert diluents commonly used in the art, such as water or other solvents, solubilizing agents and emulsifiers, e.g. ethyl alcohol, isopropyl alcohol, ethyl carbonate, ethyl acetate, benzyl alcohol, benzyl benzoate, propylene glycol, 1,3-butylene glycol, dimethylformamide, oils (after checking that the potentially radioprotective effect of these does not prevent the desired effect under radiation), in particular cottonseed oil, peanut oil, corn germ oil, olive oil, castor oil and sesame oil, glycerol, tetrahydrofurfuryl alcohol, polyethylene glycols and sorbitan fatty acid esters or mixtures of these substances, and the like.

"Patient" includes both a human and other mammals.

"Pharmaceutical composition" means a composition comprising a compound of formula I and at least one component selected from the group consisting of pharmaceutically acceptable carriers, diluents, adjuvants, excipients, or vehicles, such as preservatives, fillers, wetting agents, emulsifying agents, suspending agents, antibacterial agents, antifungal agents, lubricating agents, and dispersing agents, depending on the nature of the mode of administration and the dosage forms Examples of suspending agents include ethoxylated isostearyl alcohols, polyoxyethylene sorbitol and sorbitan esters, microcrystalline cellulose, aluminium metahydroxide, bentonite, agar-agar and tragacanth, or mixtures of these substances. Prevention of the action of microorganisms can be provided by various antibacterial and antifungal agents, e.g. parabens, chlorobutanol, phenol, sorbic acid, and the like. It may also be desirable to include isotonic agents, for example sugars, sodium chloride, and the like. Examples of suitable carriers, diluents, solvents or vehicles include water, ethanol, polyols, suitable mixtures thereof, vegetable oils (such as olive oil), and injectable organic esters such as ethyl oleate.

"Pharmaceutically acceptable" means that it is, within the scope of sound medical judgement, suitable for use in contact with human and lower animal cells without undue toxicity, irritation, allergic response or the like, and is commensurate with a reasonable risk/benefit ratio.

The term "pharmaceutically acceptable salts" refers to the relatively non-toxic inorganic and organic acid addition salts and base addition salts of the compounds of the present invention. These salts can be prepared in situ during the final isolation and purification of the compounds. In particular, acid addition salts can be prepared by separately reacting the purified compound in its purified form with an organic or inorganic acid and isolating the resulting salt. Examples of acid addition salts include the salts described by, for example, S. M. Berge et al. "Pharmaceutical Salts" J. Pharm. Sci, 66: p. 1-19 (1977). Acid addition salts can also be prepared by separately reacting the purified compound in its acid form with an organic or inorganic base and isolating the resulting salt. Suitable inorganic base addition salts are prepared from metal bases which include sodium hydride, sodium hydroxide, potassium hydroxide, calcium hydroxide, aluminium hydroxide, lithium hydroxide, magnesium hydroxide, and zinc hydroxide. Suitable base amino addition salts are prepared from amines that have sufficient alkalinity to form a stable salt, and preferably include those amines that are often used in medicinal chemistry due to their low toxicity and acceptability for medical use.

It should be understood that the present invention covers all suitable combinations of the particular and preferred groupings mentioned herein.

According to another object, the present invention also relates to the method for preparing the compounds of formula (I), said method comprising:

the step of complexing the compound of formula (II):

[Chem 6]

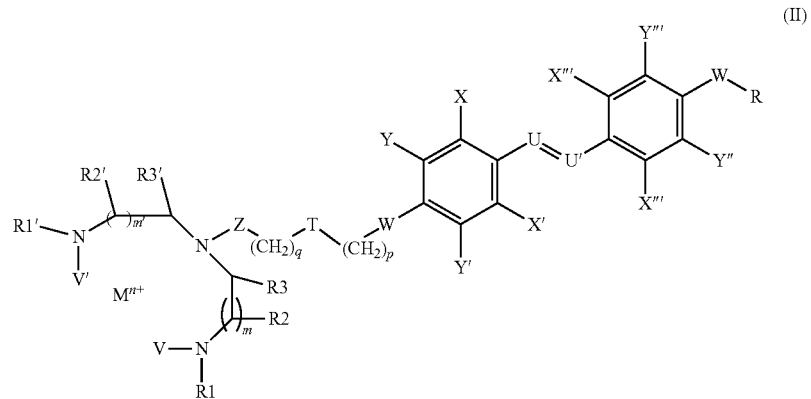

(II)

In which:
R1, R2, R3, V, m, R1', R2', R3', V, m', Z, T, q, p, W, W, X, X', X", X''', Y, Y', Y", Y''', R, U, U' are as defined above,
In the form of cis and/or trans isomers and mixtures thereof;
with a precursor of the metal M, and
the possible UV irradiation of the product obtained, in order to predominantly obtain the cis isomer.

Complexing with the metal agent M can generally be carried out in a solvent such as water, at a temperature between room temperature and the reflux temperature of the reaction mixture, for example between 40 and 100° C. Typically, the pH of the solution is maintained between 5 and 7.

According to one embodiment, the compound of formula (II) has the formula (IIA):

[Chem 7]

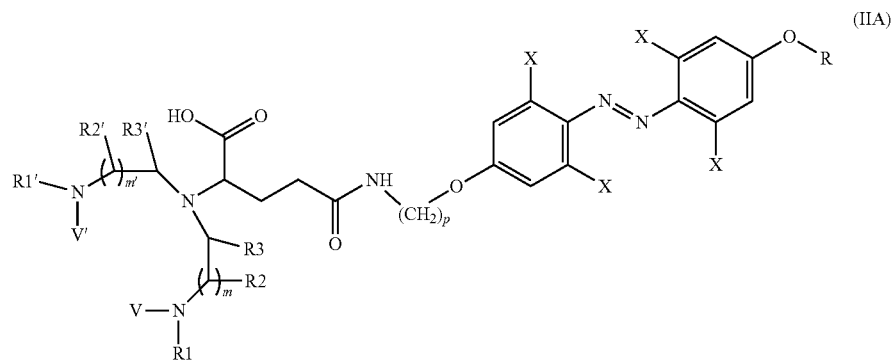

(IIA)

In which R1, R2, R3, V, m, R1, R2', R3', V, m', p, X, R are defined as in formula (I).

According to one embodiment, the compound of formula (II) has the formula (IIB):

[Chem 8]

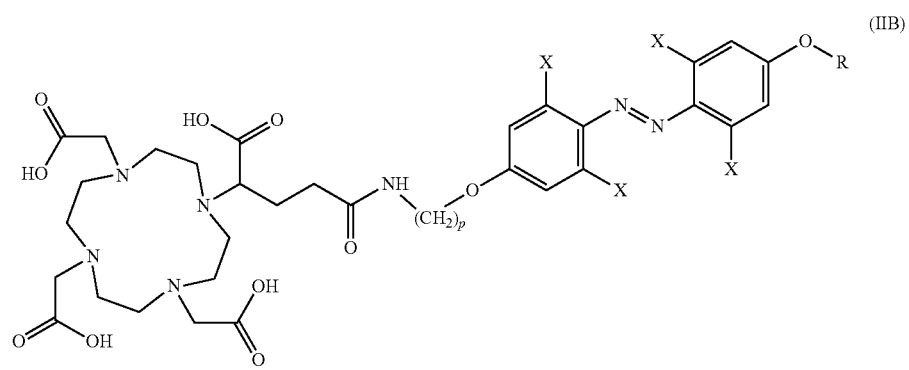

(IIB)

In which p, X, R are defined as in formula (I).

According to one embodiment, the compound of formula (II) has the formula (IIC):

[Chem 9]

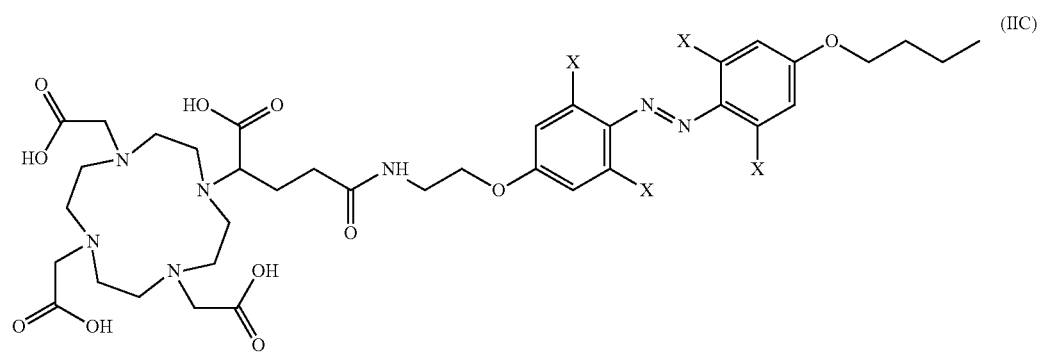

(IIC)

In which X is defined as in formula (I).

According to one embodiment, the compound of formula (II) is obtained by coupling a compound of formula (III) and a compound of formula (IV):

[Chem 10]

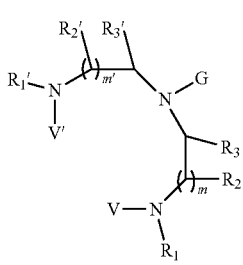
(III)

[Chem 11]

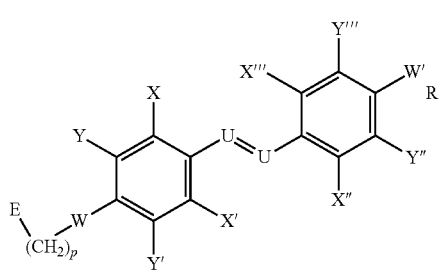
(IV)

In which:

R1, R2, R3, V, m, R1', R2', R3', V', m', Z, T, q, p, W, W', X, X', X'', X''', Y, Y', Y'', Y''', R, U, U' are as defined above; and E is a straight or branched C1-C10 alkyl or alkoxy chain, a cycloalkyl or aryl group, optionally comprising one or more heteroatoms selected from N, O or S, optionally integrating or substituted with one or more substituents independently selected from halogen atoms, and anhydride, carboxy, nitrile, nitro, thio, amino, amido, aryl, heteroaryl, hydroxyl, ester, carboxylic acid or carboxylate groups provided that E contains a nucleophilic substituent such as a hydroxyl, thiol or primary or secondary amine function to effect the coupling to the molecule (III).

G is a straight or branched C1-C10 alkyl or alkoxy chain, a cycloalkyl or aryl group, optionally comprising one or more heteroatoms selected from N, O or S, optionally substituted with one or more substituents independently selected from halogen atoms, and anhydride, carboxy, nitrile, nitro, thio, amino (primary or secondary), amido, aryl, heteroaryl, hydroxyl, carboxylic acid or carboxylate groups, it being understood that G contains an electrophilic substituent such as an activated carboxylic acid function or an anhydride function in order to carry out the coupling to the molecule (IV).

The coupling reaction may be carried out in the presence of a base, in particular an organic base such as triethylamine for example. The reaction can be conducted under anhydrous conditions.

According to one embodiment, the compound of formula (III) has the formula (IIIA):

[Chem 12]

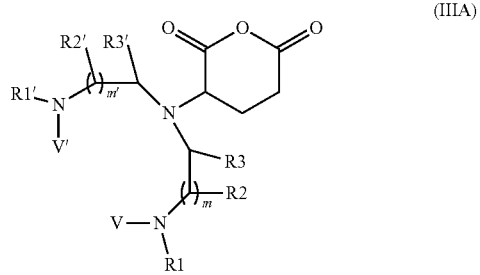
(IIIA)

In which R1, R2, R3, V, m, R1', R2', R3', V', m', are as defined above.

According to one embodiment, the compound of formula (III) has the formula (IIIB):

[Chem 13]

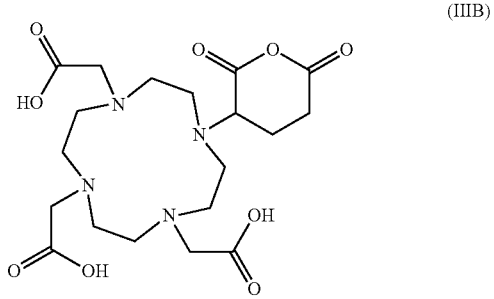
(IIIB)

According to one embodiment, the compound of formula (IV) has the formula (IVA):

[Chem 14]

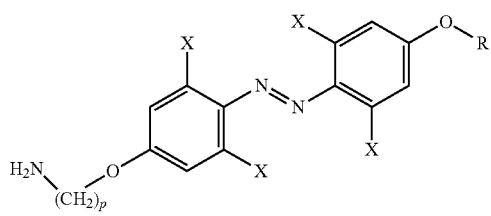
(IVA)

In which p, X, R are as defined in formula (I).

According to one embodiment, the compound of formula (IV) has the formula (IVB):

[Chem 15]

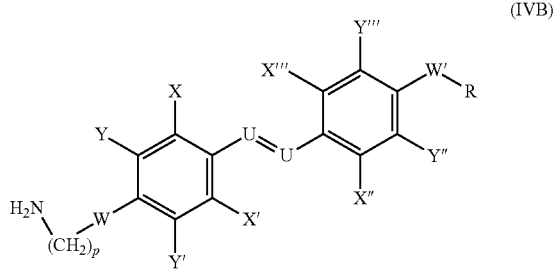

(IVB)

In which p, W, W', X, X', X'', X''', Y, Y', Y'', Y''', R, U, U' are as defined above. According to one embodiment, the compound of formula (IV) has the formula (IVC):

[Chem 16]

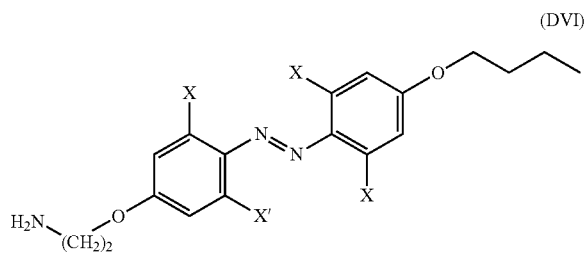

(DVI)

In which X is as defined in formula (I).

Compounds of formula (III) are generally commercial. In particular, the compound of formula (IIIB) is the compound DOTAGA.

Compounds of formula (IV) can be prepared by applying and/or adapting the synthetic method described below in the examples.

In general, the starting products and intermediates of the compounds useful in the invention can be prepared by the application or adaptation of known methods heretofore in use or described in the literature, for example those described by R. C. Larock in Comprehensive Organic Transformations, VCH Publishers, 1989.

In reactions, it may be necessary to protect reactive functional groups, e.g. hydroxy, amino, imino, thio, and carboxy groups, when they are desired in the final product, to avoid their undesirable involvement in the reactions. Traditional protection groups can be used according to standard practice; for examples see T. W. Green and P. G. M. Wuts in "Protective Groups in Organic Chemistry", John Wiley and Sons, 1991; J. F. W. McOmie in "Protective Groups in Organic Chemistry", Plenum Press, 1973.

Unless specifically stated, there is no particular restriction on the nature of the solvent to be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, in particular fatty acid amides, such as dimethylformamide, and ethers, such as diethyl ether and tetrahydrofuran.

Reactions can take place at a wide range of temperatures, typically between about 0° C. and 150° C. (preferably between about room temperature and about 100° C.). The time required for the reaction can also vary considerably, depending on many factors, including the reaction temperature and the nature of the reagents.

The compounds thus prepared can be recovered from the reaction mixture by conventional means. For example, the compounds can be recovered by distilling the solvent from the reaction mixture or if necessary after distilling the solvent from the solution mixture, pouring the remainder into water followed by extraction with a water-immiscible organic solvent, and distilling the solvent from the extract. In addition, the product can, if desired, be further purified by various techniques, such as recrystallization, reprecipitation or various chromatographic techniques, including column chromatography or preparative thin-layer chromatography.

Acid addition salts can be formed with useful compounds according to the invention in which a base function such as an amino, alkylamino or dialkylamino group is present. Pharmaceutically acceptable, i.e. non-toxic, acid addition salts are preferred. The selected salts are optimally chosen to be compatible with the usual pharmaceutical vehicles and suitable for parenteral administration. The acid addition salts of the compounds useful in the present invention can be prepared by reaction of the free base with the appropriate acid, by the application or adaptation of known methods. For example, the acid addition salts of the compounds useful in this invention can be prepared either by dissolving the free base in water or in an aqueous alcoholic solution or suitable solvents containing the appropriate acid and isolating the salt by evaporating the solution, or by reacting the free base and the acid in an organic solvent, in which case the salt separates directly or can be obtained by concentration of the solution. The acid addition salts of the compounds useful in this invention can be regenerated from the salts by the application or adaptation of known methods. For example, the parent compounds useful in the invention can be regenerated from their acid addition salts by treatment with an alkali, for example an aqueous sodium bicarbonate solution or an aqueous ammonia solution.

The useful compounds according to this invention can be regenerated from their base addition salts by the application or adaptation of known methods. For example, useful parent compounds according to the invention can be regenerated from their base addition salts by treatment with an acid, for example hydrochloric acid.

Base addition salts can be formed when the useful compound according to the invention contains a carboxyl group. Bases which may be used to prepare base addition salts preferably include those which produce, when combined with a free acid, pharmaceutically acceptable salts, i.e. salts whose cations are not toxic to the patient in the pharmaceutical doses of the salts, so that the beneficial inhibitory effects inherent in the free base are not cancelled out by the side effects attributable to the cations. Pharmaceutically acceptable salts, including those derived from alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methylglucamine, lysine arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide and analogues.

The useful compounds according to the present invention can be readily prepared, or formed during the method of the invention, as solvates (e.g. hydrates). Hydrates of the compounds useful in the present invention can be easily prepared by recrystallization of an aqueous/organic solvent mixture, using organic solvents such as dioxan, tetrahydrofuran or methanol.

FIGURES

FIG. 1 shows the absorbance spectra of cis-GdAzo (a) and cis-GdFAzo (d) under gamma irradiation in PBS. PPS1: Photostationary state containing the predominantly cis isomer. b, e: Histograms representing the molecular activation of cis-GdAzo and cis-Azo (control molecule without Gd) (b) or of cis-GdFAzo and cis-FAzo control molecule without Gd) (e) under gamma irradiation in PBS determined by HPLC and calculated by the difference in the proportion of trans-isomer in the medium (n=3). c: Molecular activation of cis-GdAzo and cis-GdFAzo under X-ray, gamma and Linac linear electron accelerator. f: Histogram representing the molecular activation of cis-MAzo (M being the metal indicated on the X-axis) under gamma irradiation in PBS determined by HPLC and calculated by the difference in the proportion of trans isomer in the medium (n=3). Gy: Gray $(J.L^{-1})$. XR: X-ray irradiation. GR: Gamma ray irradiation. E: Irradiation by Linac linear electron accelerator. NI: Not irradiated. Standard deviations are plotted on the graphs. *** $P<0.001$ (Two-way Anova with Bonferroni post-test).

Figure 2:
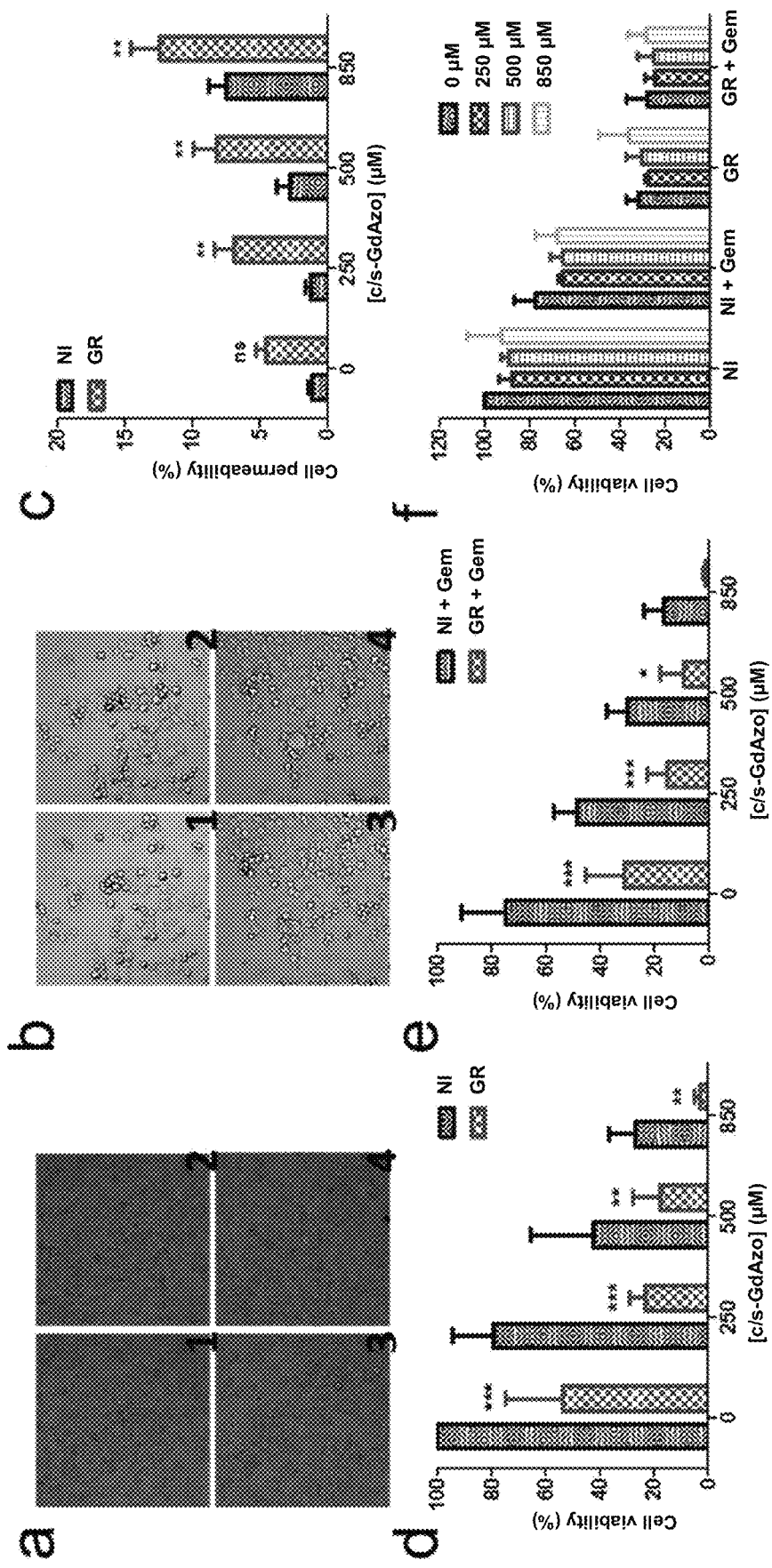

FIG. 2 shows a: Microscopy images of cancer cells (Panc-1, human pancreatic cancer) in the presence of propidium iodide and the inactive compound cis-GdAzo (1, 2) or the active compound trans-GdAzo (3, 4) at a concentration of 500 PM before (1, 3) or 30 min after (2, 4) the introduction of the compounds. Superposition of white light and fluorescence images (propidium iodide in the nuclei appears in red and shows membrane permeabilization). b: Microscopy images of cancer cells (Panc-1) in the presence of propidium iodide and the inactive compound cis-GdAzo at a concentration of 250 µM (1, 2) or 500 µM (3, 4), before (1, 3) or 30 min after (2, 4) irradiation of the medium under gamma radiation (2 Gy). c: Histogram comparing the impact of gamma irradiation (2 Gy) on cell permeabilization (Panc-1) in the presence of propidium iodide and cis-GdAzo (n=3). d, e: Histograms comparing the impact of gamma irradiation (2 Gy) on the mortality of Gem-resistant cancer cells (CCRF-CEM ARAC-8C, human acute lymphoblastic leukemia) 4 days after treatment in the presence of cis-GdAzo (d) or in the presence of cis-GdAzo and Gem (0.1 µM) (e) for a duration of 1 h. f: Histogram comparing the impact of gamma irradiation (2 Gy) on the mortality of Gem-resistant cancer cells (CCRF-CEM ARAC-8C) in the presence of Dotarem® or Dotarem® and Gem (0.1 µM). Gy: Gray $(J.L^{-1})$. GR: Gamma ray irradiation. NI: Not irradiated. The standard errors of the mean are plotted in graph c and the standard deviations are plotted in graphs d-f. * $P<0.05$,  $P<0.01$, * $P<0.001$ (Two-way Anova with Bonferroni post-test).

EXAMPLES

1. Analytical Chromatography Methods

Method A

HPLC (high-performance liquid chromatography) analyses were performed on a 1565 binary HPLC pump (Waters), PAD 2998 reader (Waters), with an Agilent Eclipse XDB-C18 reversed-phase column (length: 250 mm, diameter: 4.6 mm, stationary phase: 5 µm) using a 0.05% water-TFA/ 0.05% acetonitrile-TFA gradient system; 0' (98/2), 5' (98/2), 25' (0/100), 27' (0/100), 29' (98/2), 35' (98/2) at a flow rate of 1 mL·min$^{-1}$ (30 µL injected) The data was processed on Empower.

Method B

LCMS (liquid chromatography mass spectrometry) analyses were performed on an Alliance 2695 system (Waters) with an XBridge C18 reversed-phase column (length: 150 mm, diameter: 2.1 mm, stationary phase: 3.5 µm) using a 0.1% water-FA/acetonitrile gradient system; 0' (95/5), 20' (0/100) at a flow rate of 0.25 mL·min$^{-1}$ (10 µL injected). The mass analyser was a TOF LCT Premier (Waters). The capillary voltage was 2.8 kV. The cone voltage was 35 V. The source temperature was 120° C. and the desolvation temperature was 280° C. The data was processed on MassLynx.

Method C

HPLC analyses were performed on a 2525 binary HPLC pump (Waters) coupled to a 515 HPLC pump (Waters), PAD 2996 reader (Waters), with an XBridge C18 reversed-phase column (length: 100 mm, diameter: 3.0 mm, stationary phase: 3.5 µm) using a 0.05% water-TFA/acetonitrile isocratic system at a flow rate of 0.75 mL·min$^{-1}$ (10 µL injected). The detection wavelength corresponded to the isobestic point of the compound studied in the mobile phase used. The data was processed on MassLynx.

II. Summaries

General

All reagents were purchased from Sigma-Aldrich or Alfa Aesar with the highest purity available and were used without further purification. The DOTAGA anhydride was purchased from CheMatech and was used without further purification. The silica gel (Aldrich 717185 Si 60, 40-63 µm) used for the flash chromatography was purchased from VWR. RP-18 reversed-phase flash chromatography was performed on a CombiFlash instrument (Biotage). Thin-layer chromatography was carried out using aluminium foil coated with 60F254 silica gel (detection by UV lamp at 254 nm or by ninhydrin). The $^1H$, $^{13}C$ et $^{19}F$ NMR spectra were acquired on Bruker 300 MHz or 400 MHz spectrometers at ambient temperature. Chemical shifts δ are given in ppm using the solvent as a reference. The coupling constants J are measured in Hz. The coupling profiles are described by the abbreviations d (doublet), t (triplet) and m (mutiplet). High resolution mass spectrometry (HRMS) experiments were performed in a 3/7 H$_2$O/methanol mixture by electrospray ionization in positive mode, unless otherwise indicated, using a time-of-flight mass analyser with a TOF-LCT Premier mass spectrometer (Waters). The analytical chromatography methods (HPLC and LCMS) are described in a dedicated paragraph. The purity of the synthetic intermediates was determined by $^1H$ NMR or reversed-phase HPLC. The purity of the final products was determined by reversed-phase HPLC and was confirmed to be >95%.

The following compounds were synthesized:
[Chem 17]
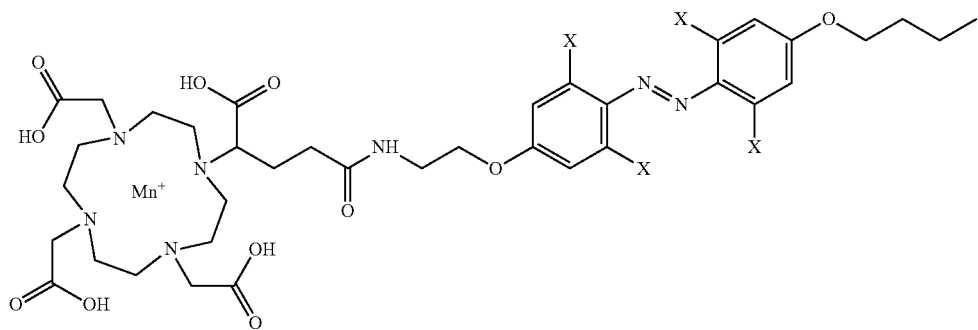
Where X=H or F,
Where M=Cu, Ga, Y, In, Eu, Gd, Yb or Bi,
Where n=2 or 3
according to the following synthesis scheme:
[Chem 18]
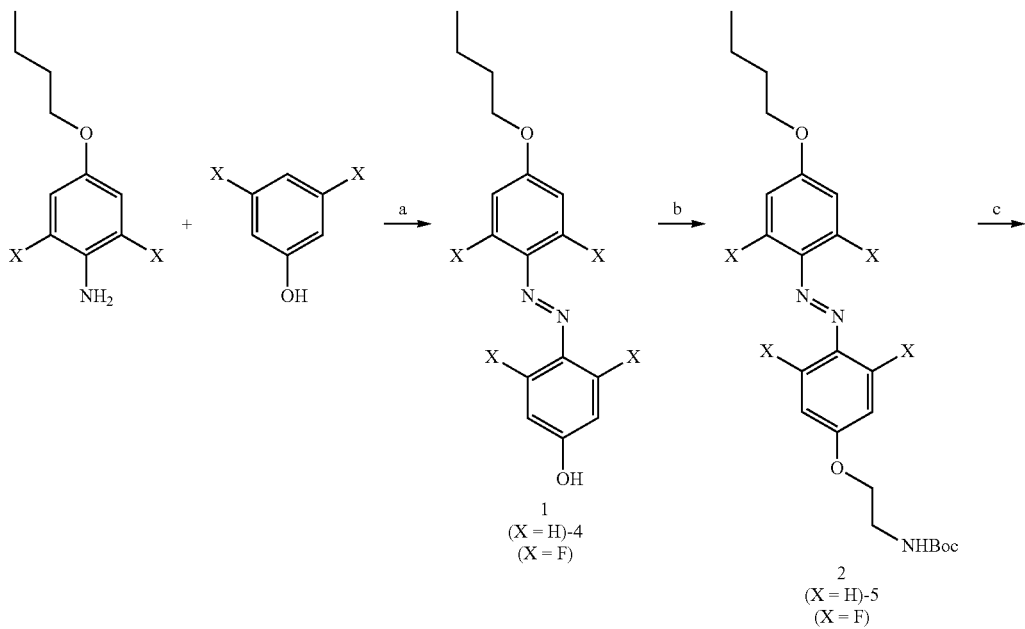

-continued
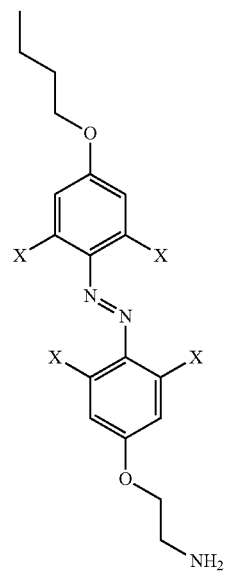
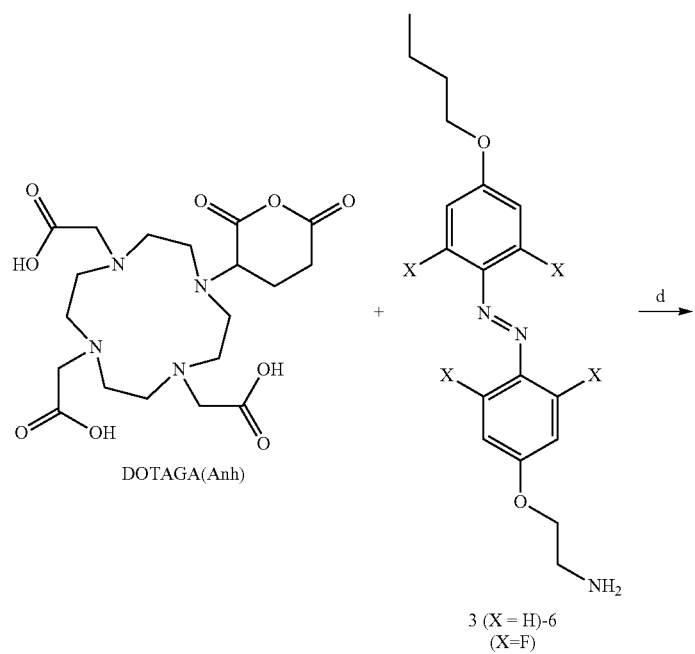

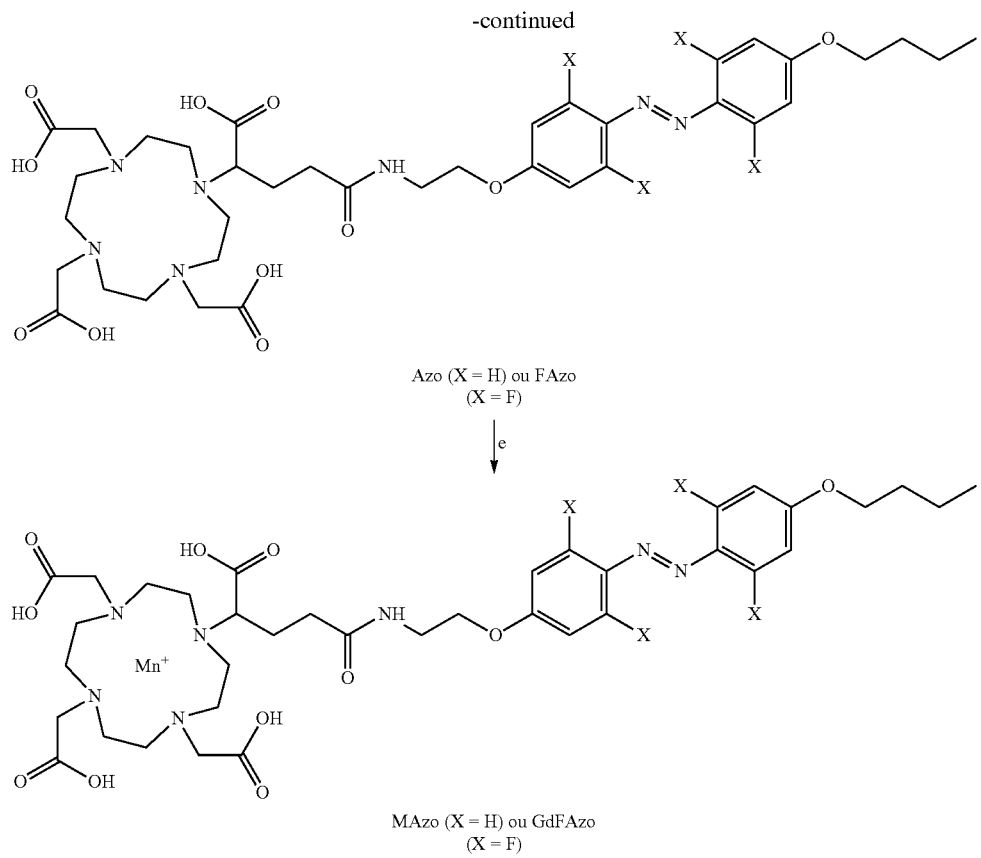

Azo (X = H) ou FAzo
(X = F)

↓ e

MAzo (X = H) ou GdFAzo
(X = F)

Synthesis of 4-hydroxy-4'-butoxyazobenzene (1)

4-Butoxyaniline (2.00 mL, 12.0 mmol) and sodium nitrite (0.854 g, 12.0 mmol, 1.0 equiv) were dissolved in a 1:1 EtOH/$H_2$O mixture (24 mL) and the medium was cooled to 0° C. Ice (12 g) was introduced into the medium before the careful addition of cc HCl (2.6 mL). A previously prepared aqueous solution (6.3 mL) of phenol (1.14 g, 12.0 mmol, 1.0 equiv) and NaOH (0.960 g, 24.0 mmol, 2.0 equiv) cooled to 0° C. was carefully introduced into the medium at 0° C. The medium was stirred for 20 min at 0° C. and then for 70 min at ambient temperature (AT). After adjusting the pH to 1 (cc HCl), the medium was left to stand for 30 min at AT before filtration. The precipitate was washed with water (4×50 mL), solubilized in DCM and the organic phase was dried over $MgSO_4$ before being concentrated. 4-hydroxy-4'-butoxyazobenzene 1 (2.76 g, 10.2 mmol, 85%) was isolated as a black amorphous powder.

$^1$H NMR (400 MHz; $CDCl_3$) δ (ppm): 7.87 (d; J=8.9 Hz; 2H); 7.82 (d; J=8.8 Hz; 2H); 6.98 (d; J=8.9 Hz; 2H); 6.91 (d; J=8.8 Hz; 2H); 4.03 (t; J=6.5 Hz; 2H); 1.85-1.75 (m; 2H); 1.58-1.45 (m; 2H); 0.99 (t; J=7.4 Hz; 3H).

$^{13}$C NMR (75 MHz; $CDCl_3$) δ (ppm): 161.51; 158.38; 146.89; 146.63; 124.81; 124.56; 116.07; 114.92; 68.22; 31.35; 19.33; 13.96.

HRMS (m/z): calculated for $C_{16}H_{19}N_2O_2$; 271.1447 ([M+H]$^+$). Found 271.1440.

$R_f$=0.36 ($SiO_2$; DCM; UV).

Synthesis of 4-(N-(tert-butyloxycarbonyl)-ethoxyamine)-4'-butoxyazobenzene (2)

4-Hydroxy-4'-butoxyazobenzene 1 (2.00 g, 7.40 mmol) and $K_2CO_3$ (1.53 g, 11.1 mmol, 1.5 equiv) were dissolved in acetone (25 mL). After 30 min stirring at AT under argon, 2-(Boc-amino)ethyl bromide (4.98 g, 22.2 mmol, 3.0 equiv) was introduced into the medium. After stirring at reflux for 18 h, the medium was filtered off while hot and the precipitate was washed with hot acetone (75 mL). The filtrate was left to stand at AT for 30 min before filtration and the resulting precipitate 1 was washed with cold acetone. The filtrate was left to stand at 0° C. for 3 h before filtration. The resulting precipitate 2 was washed with cold acetone and added to precipitate 1. The filtrate was concentrated and purified by flash chromatography on silica (DCM). 4-(N-(tert-butyloxycarbonyl)-ethoxyamine)-4'-butoxyazobenzene 2 (2.27 g, 5.49 mmol, 74%) was isolated as a yellow amorphous powder (57% by precipitation, 17% by flash chromatography).

$^1$H NMR (400 MHz; $CDCl_3$) δ (ppm): 7.86 (2d; J=8.9 Hz; 4H); 6.99 (2d; J=8.9 Hz; 4H); 4.10 (t; J=5.0 Hz; 2H); 4.04 (t; J=6.5 Hz; 2H); 3.57 (m; 2H); 1.87-1.74 (m; 2H); 1.64-1.40 (m; 11H); 1.00 (t; J=7.4 Hz; 3H).

$^{13}$C NMR (100 MHz; $CDCl_3$) δ (ppm): 161.46; 160.62; 156.03; 147.51; 147.07; 124.52; 124.48; 114.84; 114.82; 79.79; 68.18; 67.64; 40.27; 31.42; 28.55; 19.38; 13.98.

HRMS (m/z): calculated for $C_{23}H_{32}N_3O_4$; 414.2393 ([M+H]$^+$). Found 414.2396.

$R_f$=0.90 ($SiO_2$; DCM/MeOH 98:2; UV).

Synthesis of 4-aminoethoxy-4'-butoxyazobenzene (3)

4-(N-(tert-butyloxycarbonyl)-ethoxyamine)-4'-butoxyazobenzene 2 (1.26 g, 3.04 mmol) was dissolved in a 4:1 DCM/TFA mixture (63 mL) and the medium was stirred for 1.5 h at AT. After concentration, diethyl ether (250 mL) was introduced and the precipitate formed was concretized for 1 h before filtration and washing with diethyl ether (4×50 mL). 4-aminoethoxy-4'-butoxyazobenzene 3 (1.25 g, 2.93 mmol, 96%, TFA salt) was isolated as a yellow amorphous powder.

$^1$H NMR (400 MHz; MeOD) δ (ppm): 7.88 (d; J=8.9 Hz; 2H); 7.85 (d; J=8.9 Hz; 2H); 7.15 (d; J=8.9 Hz; 2H); 7.04 (d; J=8.9 Hz; 2H); 4.32 (t; J=4.4 Hz; 2H); 4.06 (t; J=6.4 Hz; 2H); 3.41 (t; J=4.4 Hz; 2H); 1.86-1.73 (m; 2H); 1.60-1.46 (m; 2H); 1.00 (t; J=7.4 Hz; 3H).

$^{13}$C NMR (75 MHz; MeOD) δ (ppm): 163.03; 161.34; 148.97; 148.10; 125.42; 125.30; 115.99; 115.80; 69.12; 65.59; 40.24; 32.43; 20.28; 14.16.

HRMS (m/z): calculated for $C_{18}H_{24}N_3O_2$; 314.1869 ([M+H]$^+$). Found 314.1864.

HPLC (method A); $t_R$ 17.92 min(cis)-20.35 min(trans).

$R_f$=0.70 (SiO$_2$; DCM/MeOH 95:5; UV or ninhydrin).

Synthesis of 4-(N-(1,4,7,10-tetraazacyclododecane-1,4,7-triacetic acid-10-glutaryl)-ethoxyamine)-4'-butoxyazobenzene (Azo)

4-aminoethoxy-4'-butoxyazobenzene 3 (259 mg, 0.606 mmol, TFA salt) was dissolved in anhydrous DMF (4.3 mL). After introduction of triethylamine (253 µL, 1.81 mmol, 3.0 equiv), the medium was stirred for 5 min at AT under argon. The DOTAGA anhydride (278 mg, 0.606 mmol, 1.0 equiv) was then introduced and the medium was stirred for 21 h at 70° C. under argon. After concentration, diethyl ether (100 mL) was introduced and the precipitate formed was concretized for 30 min before filtration and washing with diethyl ether (2×50 mL). The crude was purified by reverse phase flash chromatography (RP-18, Biotage, gradient H$_2$O 0.05% FA/CH$_3$CN 0.05% FA 1:0 to 2:8). 4-(N-(1,4,7,10-tetraazacyclododecane-1,4,7-tri-acetic acid-10-glutaryl)-ethoxyamine)-4'-butoxyazobenzene Azo (294 mg, 0.381 mmol, 63%) was isolated by freeze-drying in the form of a yellow electrostatic powder.

HRMS (m/z): calculated for $C_{37}H_{54}N_7O_{11}$; 772.3881 ([M+H]$^+$). Found 772.3883.

LCMS (method B); $t_R$ 12.357 min(cis)-14.437 min(trans).

Synthesis of 2,6-difluoro-4-hydroxy-2',6'-difluoro-4'-butoxyazobenzene (4)

2.6-difluoro-4-butoxyaniline (2.20 g, 10.9 mmol) and sodium nitrite (0.755 g, 10.9 mmol, 1.0 equiv) were dissolved in a 1:1 EtOH/H$_2$O mixture (22 mL) and the medium was cooled to 0° C. Ice (11 g) was introduced into the medium before the careful addition of cc HCl (2.37 mL). A previously prepared aqueous solution (5.7 mL) of 3,5-difluorophenol (1.42 g, 10.9 mmol, 1.0 equiv) and NaOH (0.876 g, 21.9 mmol, 2.0 equiv) cooled to 0° C. was carefully introduced into the medium at 0° C. The medium was stirred for 20 min at 0° C. and then for 70 min at AT. After adjusting the pH to 1 (cc HCl), the medium was left to stand for 30 min at AT before filtration. The precipitate was washed with water (4×50 mL), solubilized in DCM and the organic phase was dried over MgSO$_4$ before being concentrated. The residue (black viscous liquid) was concentrated under a vacuum manifold (3.15 g) and was used without further purification in the next step.

$^1$H NMR (400 MHz; DMSO) δ (ppm): 6.93 (d; JH-F=11.4 Hz; 2H); 6.64 (d; JH-F=11.4 Hz; 2H); 4.09 (t; J=6.5 Hz; 2H); 1.77-1.66 (m; 2H); 1.49-1.38 (m; 2H); 0.94 (t; J=7.4 Hz; 3H)

$^{13}$C NMR (101 MHz; DMSO) δ (ppm): 161.40 (t; $J_{C-F}$=14.8 Hz); 161.11 (t; $J_{C-F}$=14.8 Hz); 157.69 (dd; $J_{C-F}$=39.1; 7.7 Hz); 155.13 (dd; $J_{C-F}$=38.2; 7.8 Hz); 125.00 (t; $J_{C-F}$=10.2 Hz) 124.05 (t; $J_{C-F}$=10.3 Hz); 100.26 (dd; $J_{C-F}$=22.6; 2.0 Hz); 99.68 (dd; $J_{C-F}$=24.2; 2.1 Hz); 68.74 (s); 30.31 (s); 18.55 (s); 13.58 (s).

$^{19}$F NMR (376 MHz; DMSO; decoupled) δ (ppm): −118.99; −119.27.

$^{19}$F NMR (376 MHz; DMSO) δ (ppm): −118.99 (d; $J_{F-H}$=12.1 Hz); −119.27 (d; $J_{F-H}$=12.0 Hz).

HRMS (m/z): calculated for $C_{16}H_{15}F_4N_2O_2$; 343.1070 ([M+H]$^+$). Found 343.1060.

$R_f$=0.20 (SiO$_2$; cyclohexane/ethyl acetate 9:1; UV).

Synthesis of 2,6-difluoro-4-(N-(tert-butyloxycarbonyl)-ethoxyamine)-2',6'-difluoro-4'-butoxyazobenzene (5)

2,6-difluoro-4-hydroxy-2',6'-difluoro-4'-butoxyazobenzene 4 (2.18 g crude, 6.37 mmol considered) and K$_2$CO$_3$ (1.32 g, 9.57 mmol, 1.5 equiv) were dissolved in acetone (22 mL). After 30 min stirring at AT under argon, 2-(Boc-amino) ethyl bromide (4.29 g, 19.1 mmol, 3.0 equiv) was introduced into the medium. After stirring at reflux for 18 h, the medium was concentrated and purified by flash chromatography on silica (cyclohexane/ethyl acetate, gradient 1/0 to 7/3). 2,6-difluoro-4-(N-(tert-butyloxycarbonyl)-ethoxyamine)-2',6'-difluoro-4'-butoxyazobenzene 5 (624 mg, 1.28 mmol, 17% on 2 steps) was isolated as an amorphous yellow powder.

$^1$H NMR (400 MHz; DMSO) δ (ppm): 7.04 (s; 1H); 6.95 (d; JH-F=11.8 Hz; 4H); 4.10 (m; 4H); 3.34-3.26 (m; 2H); 1.75-1.67 (m; 2H); 1.49-1.39 (m; 2H); 1.38 (s; 9H); 0.94 (t; J=7.4 Hz; 3H).

$^{13}$C NMR (101 MHz; DMSO) δ (ppm): 161.53 (t; $J_{C-F}$=14.3 Hz); 161.16 (t; $J_{C-F}$=14.2 Hz); 157.59 (t; $J_{C-F}$=7.9 Hz); 155.64 (s); 155.03 (t; $J_{C-F}$=7.7 Hz); 125.09 (t; $J_{C-F}$=8.3 Hz); 124.90 (t; $J_{C-F}$=8.3 Hz); 99.90 (dd; $J_{C-F}$=11.3; 1.7 Hz); 99.67 (dd; $J_{C-F}$=11.3; 1.7 Hz); 77.86 (s); 68.80 (s); 67.87 (s); 38.71 (s); 30.29 (s); 28.17 (s); 18.53 (s); 13.57 (s)

$^{19}$F NMR (376 MHz; DMSO; decoupled) δ (ppm): −118.79; −118.85.

$^{19}$F NMR (376 MHz; DMSO) δ (ppm): −118.79 (d; $J_{F-H}$=12.0 Hz); −118.85 (d; $J_{F-H}$=11.9 Hz).

HRMS (m/z): calculated for $C_{23}H_{28}F_4N_3O_4$; 486.2016 ([M+H]$^+$). Found 486.2015.

$R_f$=0.30 (SiO$_2$; cyclohexane/ethyl acetate 8:2; UV).

Synthesis of 2,6-difluoro-4-aminoethoxy-2',6'-difluoro-4'-butoxyazobenzene (6)

2,6-difluoro-4-(N-(tert-butyloxycarbonyl)-ethoxyamine)-2,6-difluoro-4'-butoxyazobenzene 5 (879 mg, 1.81 mmol) was dissolved in a 4:1 DCM/TFA mixture (37 mL) and the medium was stirred for 1.5 h at AT. After concentration, diethyl ether (200 mL) was introduced and the precipitate 1 formed was concretized for 1 h before filtration and washing with diethyl ether (4×100 mL). The filtrate was concentrated and a viscous precipitate 2 was formed in n-hexane (200 mL), filtered and washed with n-hexane (3×200 mL). Precipitates 1 and 2 were dried under a vacuum manifold. 2,6-difluoro-4-aminoethoxy-2',6'-difluoro-4'-butoxyazobenzene 6 (858 mg, 1.72 mmol, 95%, TFA salt) was isolated as an amorphous yellow powder (precipitate 1, 70%) and a yellow oil (precipitate 2, 25%).

$^1$H NMR (400 MHz; DMSO) δ (ppm): 7.98 (s; 3H); 7.00 (d; $J_{H-F}$=11.3 Hz; 2H); 6.96 (d; $J_{H-F}$=11.8 Hz; 2H); 4.30 (t; J=5.0 Hz; 2H); 4.11 (t; J=6.5 Hz; 2H); 3.26 (t; J=5.0 Hz; 2H); 1.80-1.63 (m; 2H); 1.53-1.33 (m; 2H); 0.94 (t; J=7.4 Hz; 3H).

$^{13}$C NMR (101 MHz; DMSO) δ (ppm): 161.76 (t; $J_{C-F}$=14.4 Hz); 160.27 (t; $J_{C-F}$=14.0 Hz); 157.57 (dd; $J_{C-F}$=25.8; 7.6 Hz); 155.00 (dd; $J_{C-F}$=25.9; 7.4 Hz); 125.57 (s); 124.86 (s); 100.07 (dd; $J_{C-F}$=24.7; 2.7 Hz); 99.80 (dd; $J_{C-F}$=24.7; 2.5 Hz); 68.85 (s); 65.82 (s); 38.06 (s); 30.29 (s); 18.54 (s); 13.57 (s)

$^{19}$F NMR (376 MHz; DMSO; decoupled) δ (ppm): −73.46; −118.60; −118.74.

$^{19}$F NMR (376 MHz; DMSO) δ (ppm): −73.46 (s); −118.60 (d; $J_{F-H}$=11.9 Hz); −118.73 (d; $J_{F-H}$=11.8 Hz).

HRMS (m/z): calculated for $C_{18}H_{20}F_4N_3O_2$; 386.1492 ([M+H]$^+$). Found 386.1491.

R$_f$=0.33 (SiO$_2$; DCM/MeOH 95:5; UV or ninhydrin).

Synthesis of 2,6-difluoro-4-(N-(1,4,7,10-tetraazacyclododecane-1,4,7-triacetic acid-10-glutaryl)-ethoxyamine)-2',6'-difluoro-4'-butoxyazobenzene (FAzo)

2,6-difluoro-4-aminoethoxy-2',6'-difluoro-4'-butoxyazobenzene 6 (267 mg, 0.535 mmol, TFA salt) was dissolved in anhydrous DMF (3.8 mL). After introduction of triethylamine (223 μL, 1.60 mmol, 3.0 equiv), the medium was stirred for 5 min at AT under argon. The DOTAGA anhydride (245 mg, 0.533 mmol, 1.0 equiv) was then introduced and the medium was stirred for 21 h at 70° C. under argon. After concentration, diethyl ether (100 mL) was introduced and the precipitate formed was concretized for 30 min before filtration and washing with diethyl ether (2×50 mL). The crude was purified by reverse phase flash chromatography (RP-18, Biotage, gradient H$_2$O 0.05% FA/CH$_3$CN 0.05% FA 1:0 to 2:8). 2.6-difluoro-4-(N-(1,4,7,10-tetraazacyclododecane-1,4,7-tri-acetic acid-10-glutaryl)-ethoxyamine)-2,6-difluoro-4'-butoxyazobenzene FAzo (92.1 mg, 0.109 mmol, 20%) was isolated by freeze-drying in the form of a yellow electrostatic powder.

HRMS (m/z): calculated for $C_{37}H_{50}F_4N_7O_{11}$; 844.3504 ([M+H]$^+$). Found 844.3495.

LCMS (method B); $t_R$ 14.107 min(cis)-14.894 min(trans).

General Protocol for the Complexing of Azo and FAzo

Azo or FAzo and the metal reagent were dissolved in H2O (26 mM). After adjusting the pH to 5.5, the medium was stirred for 17 h at 50° C., ensuring that the pH remained in the range 5.5-6.0. The pH was then adjusted to 6.5 before concentration of the medium by freeze-drying and purification by reversed-phase flash chromatography (RP-18, Biotage, gradient H2O/CH3CN 1:0 to 0:1). The final product was isolated by freeze-drying as an electrostatic powder.

TABLE 1

Experimental conditions for complexation reactions.

| Metal | Starting material | Reaction scale (μmol starting material) | Type of reagent | Amount of reagent (equiv) | Yield (%) | Color of final product |
|---|---|---|---|---|---|---|
| Cu | Azo | 104 | Cu(OAc)$_2$ | 1.05 | 60 | green |
| Ga | Azo | 78.0 | GaNO$_3$ | 2.05 | 82 | yellow |
| Y | Azo | 90.0 | YCl$_3$•6H$_2$O | 1.05 | 31 | yellow |
| In | Azo | 80.0 | InCl$_3$•4H$_2$O | 1.05 | 27 | yellow |
| Eu | Azo | 130 | EuCl$_3$•6H$_2$O | 1.05 | 39 | yellow |
| Gd | Azo | 259 | GdCl$_3$•6H$_2$O | 1.05 | 88 | yellow |
| Gd | FAzo | 142 | GdCl$_3$•6H$_2$O | 1.05 | 97 | yellow |
| Yb | Azo | 110 | YbCl$_3$•6H$_2$O | 1.05 | 21 | yellow |
| Bi | Azo | 104 | BiCl$_3$* | 1.05 | 73 | yellow |

*250 mM in 6N HCl.

Copper 4-(N-(1,4,7,10-tetraazacyclododecane-1,4,7-triacetic acid-10-glutaryl)-ethoxyamine)-4'-butoxyazobenzene (CuAzo)

HRMS (m/z): calculated for $C_{37}H_{51}N_7NaO_{11}Cu$; 855.2840 ([M+Na]$^+$). Found 855.2854.

LCMS (method B); $t_R$ 13.550 min(cis)-15.934 min(trans).

Gallium 4-(N-(1,4,7,10-tetraazacyclododecane-1,4,7-triacetic acid-10-glutaryl)-ethoxyamine)-4'-butoxyazobenzene (GaAzo)

HRMS (m/z): calculated for $C_{37}H_{51}N_7O_{11}Ga$; 838.2902 ([M+H]$^+$). Found 838.2906.

LCMS (method B); $t_R$ 12.840 min(cis)-15.072 min(trans).

Yttrium 4-(N-(1,4,7,10-tetraazacyclododecane-1,4,7-triacetic acid-10-glutaryl)-ethoxyamine)-4'-butoxyazobenzene (YAzo)

HRMS (m/z): calculated for $C_{37}H_{49}N_7Na_2O_{11}Y$; 902.2344 ([M−H+2Na]$^+$). Found 902.2349.

LCMS (method B); $t_R$ 15.957 min (cis)-19.660 min (trans).

Indium 4-(N-(1,4,7,10-tetraazacyclododecane-1,4,7-triacetic acid-10-glutaryl)-ethoxyamine)-4'-butoxyazobenzene (InAzo)

HRMS (m/z): calculated for $C_{37}H_{49}N_7Na_2O_{11}In$; 928.2324 ([M−H+2Na]$^+$). Found 928.2319.

LCMS (method B); $t_R$ 15.451 min(cis)-18.899 min(trans).

Europium 4-(N-(1,4,7,10-tetraazacyclododecane-1,4,7-triacetic acid-10-glutaryl)-ethoxyamine)-4'-butoxyazobenzene (EuAzo)

HRMS (m/z) (negative mode): calculated for $C_{37}H_{49}N_7O_{11}Eu$; 920.2702 ([M−H]$^−$). Found 920.2694.

LCMS (method B); $t_R$ 13.419 min(cis)-16.718 min(trans).

Gadolinium 4-(N-(1,4,7,10-tetraazacyclododecane-1,4,7-triacetic acid-10-glutaryl)-ethoxyamine)-4'-butoxyazobenzene (GdAzo)

HRMS (m/z): calculated for $C_{37}H_{49}N_7Na_2O_{11}Gd$; 971.2527 ([M−H+2Na]$^+$). Found 971.2529.

LCMS (method B); $t_R$ 15.956 min(cis)-19.633 min(trans).

Gadolinium 2,6-difluoro-4-(N-(1,4,7,10-tetraazacyclododecane-1,4,7-triacetic acid-10-glutaryl)-ethoxyamine)-2',6'-difluoro-4'-butoxyazobenzene (GdFAzo)

HRMS (m/z): calculated for $C_{37}H_{45}F_4N_7Na_2O_{11}Gd$; 1043.2150 ([M−H+2Na]$^+$). Found 1043.2158.

LCMS (method B); $t_R$ 18.900 min(cis)-20.524 min(trans).

Ytterbium 4-(N-(1,4,7,10-tetraazacyclododecane-1,4,7-triacetic acid-10-glutaryl)-ethoxyamine)-4'-butoxyazobenzene (YbAzo)

HRMS (m/z): calculated for $C_{37}H_{49}N_7Na_2O_{11}Yb$; 987.2674 ([M−H+2Na]$^+$). Found 987.2683.

LCMS (method B); $t_R$ 16.112 min(cis)-19.968 min(trans).

Bismuth 4-(N-(1,4,7,10-tetraazacyclododecane-1,4, 7-triacetic acid-10-glutaryl)-ethoxyamine)-4'-butoxyazobenzene (BiAzo)

HRMS (m/z): calculated for $C_{37}H_{49}N_7Na_2O_{11}Bi$; 1022.3089 ([M−H+2Na]$^+$). Found 1022.3093.

LCMS (method B); $t_R$ 14.235 min(cis)-19.055 min(trans).

III. Ionizing Radiation and Cell Experiments

General

Buffer media such as phosphate buffered saline (PBS), Dulbecco's Modified Eagle Medium-high glucose (DMEM), Roswell Park Memorial Institute medium (RPMI), penicillin, streptomycin and trypan blue solution (0.4%) were purchased from Sigma Aldrich (France). Fetal bovine serum (FBS) was purchased from Gibco (France), propidium iodide (PI) was purchased from Thermo Fisher Scientific (France) and gemcitabine hydrochloride (Gem) was purchased from Sequoia Research Products (UK).

Cell Lines

Human pancreatic cancer (PANC-1) and human acute lymphoblastic leukemia (CCRF-CEM) cells were purchased from ATCC (US) and maintained as recommended by the supplier. Gem-resistant human acute lymphoblastic leukemia cells (CCRF-CEM ARAC 8C, hENT-1 receptor not expressed) were kindly provided by Dr. Buddy Ullmann (Oregon Health Sciences University). Briefly, PANC-1 cells were maintained in DMEM buffer supplemented with 10% (v/v) heat-inactivated FBS. CCRF-CEM and CCRF-CEM ARAC-8C cells were maintained in RPMI buffer supplemented with 10% (v/v) heat-inactivated FBS. All cell media were supplemented with penicillin (50 U·mL$^{-1}$) and streptomycin (0.05 mg·mL$^{-1}$). The cells were maintained in a humid atmosphere at 37° C. with 5% CO2. The cells were used before reaching the eighteenth passage and were harvested at 70-80% confluence.

Ionizing Radiation Sources

UV irradiation. UV irradiation to induce isomerization of the trans isomer to the cis isomer was carried out in a CN-15·LCchamber (Vilber Lourmat) equipped with two 15W tubes (365 nm) which provided an irradiance of 0.817 mW·cm$^{-2}$ at the irradiation position (determined by a Cole-Parmer VLX-3W microprocessor-controlled radiometer calibrated for 365 nm, Vilber Lourmat).

X-ray irradiation. X-ray irradiation was performed with an X-ray generator (Xrad 320 Dx) providing photons at an average energy of 80 keV (range 0-200 keV) at a dose rate of approximately 1 Gy/min (operation at 200 kV, 20 mA). Radiation doses are expressed in Gray.

Gamma ray irradiation. Gamma irradiation was performed with a Cesium-137 source (IBL 637) providing 662 keV photons at a dose rate of approximately 1 Gy/min. Radiation doses are expressed in Gray (1 Gy=1 J/L).

Electron beam irradiation. Electron beam irradiation was performed with a linear electron accelerator (Linac, Kinetron) delivering electrons at an energy of 4.5 MeV at a dose rate of approximately 4 Gy/min. Radiation doses are expressed in Gray.

Quantification of Ionizing-Radiation-Induced Isomerization by Absorbance Spectrophotometry and HPLC (FIG. 1)

Gd-containing compounds (GdAzo or GdFAzo) and control compounds (Azo or FAzo) (50 μM, 200 μL, PBS) were introduced into two 96-well microplates (10 wells for each compound). Both microplates were first irradiated under UV light (365 nm, 0.817 mW·cm$^{-2}$, 5 min). One microplate (plate 1) was then kept in the dark and used as a non-irradiated control while the second (plate 2) was irradiated with an increment of ionizing radiation doses (2 Gy, 3 Gy, 5 Gy and 10 Gy). After each irradiation, absorbance spectrophotometric and HPLC injection (method C) analyses were performed on the non-irradiated (plate 1) and irradiated (plate 2) compounds. A 26 min time lag between UV irradiation of plates 1 and 2 was used to allow analysis of the unirradiated control compounds (plate 1) at the same time as the ionizing irradiated compounds (plate 2) after UV irradiation. The complete experiment was performed in 4.6 h. The absorbance spectra were plotted by the mean of triplicates. The relative amount of each isomer was obtained by HPLC (detection at the isosbestic point wavelength under elution conditions) and the molecular activation (%) was determined by the difference in the proportion of trans isomer in the medium (3 independent experiments).

Confocal Microscopy without Ionizing Radiation (FIG. 2a)

The cells (PANC-1) were transferred to an imaging plate (ibiTreat 8-well micro-slide purchased from Ibidi, Germany) 24 h before the start of the experiment, and were maintained in culture medium (33000 cells in 200 μL/well) under humid atmosphere at 37° C. with 5% CO2. Immediately prior to the experiment, the cell medium was replaced with culture medium without FBS and phenol red (100 μL) and then IP (5 μL, final concentration 1 μM) was added to the medium. 15 min after the addition of the IP, a first series of images was acquired. Then the cis-GdAzoor trans-GdAzocompound (100 μL, final concentration 0 μM, 250 μM or 500 μM) was introduced into the cell medium. The imaging plate was then kept in the dark and images were acquired every 5 min for 1 h. The compound cis-GdAzo was obtained by UV irradiation (365 nm, 0.817 mW·cm$^2$, 30 min) of the compound trans-GdAzo (105 μL, 500 μM or 1 mM, cis-GdAzo>85%) in a 96-well microplate. The cells were observed with a Leica TCS SP8 gated-STED inverted microscope (Leica, Germany) using a Fluotar CS2 10×/0.30 sec HC PL objective. The instrument was equipped with a white light laser (excitation wavelength 538 nm). The red fluorescence emission was collected over a bandwidth of 560-650 nm and transmission images were obtained with the same light line and a PMT-trans detector. The pinhole was set at 1.0 Airy (73.19 μm diameter). The 16-bit digital images were obtained with the Leica SP8 LAS X software (version 2.0.1, Leica, Germany).

Confocal Microscopy in the Presence of Ionizing Radiation (FIGS. 2b-c)

Cells (PANC-1) were transferred to an imaging plate (Lab-Tek chamber slide system, glass, 8-well purchased from Thermo Fisher Scientific, France) 24 h before the start of the experiment, and were maintained in culture medium (10,000 cells in 200 μL/well) in a humid atmosphere at 37° C. with 5% CO2. Just before the experiment, the cell medium was replaced with PBS (100 μL) and IP (5 μL, final concentration 1 μM) was added to the medium. 15 min after the addition of PI, cis-GdAzo (100 μL, final concentration 0 μM, 250 μM, 500 μM or 850 μM) was introduced into the cell medium. A first series of images was acquired at this stage, and then the imaging plate was irradiated (gamma rays, 2 Gy). The imaging plate was then kept in the dark at 37° C. (plate warmer) and images were acquired every 5 min for 30 min and then every 10 min for 90 min. A similar procedure was used for the control experiment without irradiation except that the imaging plate was not irradiated with gamma rays. The cis-GdAzo compound was obtained by UV irradiation (365 nm, 0.817 mW·cm$^{-2}$, 30 min) of the trans-GdAzo compound (105 μL, 500 μM, 1 mM or 1.7 mM, cis-GdAzo>85%) in a 96-well microplate. Cells were observed with a Nikon inverted microscope (Nikon Instruments Inc., Tokyo, Japan) using a ×10 sec objective, N.A. 0.4 and equipped with a Yokogawa CSU-X1 head. The instrument was equipped with a laser diode at 561 nm as excitation wavelength. The red fluorescence emission was collected over a bandwidth of 598-672 nm and the transmission images were obtained with a white diode. The pinhole was set at 50 μm and the magnification lens at 1.2. The images were recorded by an e-Volve s-CMOS camera (Photometrics). Four images were recorded per well and two wells were used for each concentration of cis-GdAzo. Analysis of the 16-bit digital images was performed using ImageJ software (version 1.50i with the Adjustable Watershed plugin). The number of cells in the images acquired before irradiation was determined manually and the number of fluorescent cells in the images acquired before and after irradiation was calculated automatically using a script coded on ImageJ. Cell permeabilization was determined by the difference in the proportion of fluorescent cells before and 30 min after gamma irradiation (3 independent experiments).

Therapeutic Effect Under Ionizing Radiation (FIGS. 2d-f)

Just before the experiment, the cells (CCRF-CEM ARAC-8C) were dispersed in PBS and transferred to a 48-well microplate (TPP cell culture microplates purchased from Thermo Fisher Scientific, France) (40,000 cells in 80 μL/well). Gem (20 μL, final concentration 0.1 μM) or PBS (20 μL) and cis-GdAzo compound (100 μL, final concentration 0 μM, 250 μM, 500 μM or 850 μM) were added just prior to gamma irradiation of the medium (2 Gy). The medium was maintained in the dark and in a humid atmosphere at 37° C. with 5% CO2 for 1 h. Next, culture medium (600 μL) was added to each well and the cells were washed by three centrifugation cycles (300 G, 5 min, 800 μL of culture medium used for each wash). The cells were finally dispersed in culture medium (600 μL) containing or not containing Gem (final concentration 0 μM or 0.1 μM) and were maintained in a humid atmosphere at 37° C. with 5% CO2 for 4 days. The number of live cells was determined by cell count in the presence of 1:1 (v/v) trypan blue (triplicate). The experiment was repeated three times independently. Cell viability was expressed as the ratio of the number of living cells after treatment to the number of living cells without any treatment (without irradiation, in the absence of Gem and cis-GdAzo). A similar procedure was used for the control experiment without irradiation except that the 48-well microplate was not irradiated with gamma rays. A similar procedure was used for the control experiment with Dotarem® (FIG. 2f) except that Dotarem® was used instead of cis-GdAzo. The cis-GdAzo compound was obtained by UV irradiation (365 nm, 0.817 mW·cm−2, 30 min) of the trans-GdAzo compound (105 μL, 500 μM, 1 mM or 1.7 mM, cis-GdAzo>85%) in a 96-well microplate.

These results show:
(i) a new concept of activation of therapeutic molecules by the use of ionizing radiation (X-rays, gamma rays, electrons) (FIG. 1a-f). As these radiations have a very high penetration power in living tissues, this new activation concept has a strong potential for clinical use. All the organic molecules described in the literature today require the use of UV to near-IR radiation, which does not penetrate biological tissues in depth (it penetrates to a few hundred micrometres in the best of conditions).
(ii) that it is possible to activate MAzo compounds (M=Cu, Ga, Y, In, Eu, Gd, Yb, Bi) by ionizing radiation with different efficiencies depending on the metal and irradiation source used (FIGS. 1a-c,f). The GdFAzo compound can also be activated by ionizing radiation (FIGS. 1c-e). This compound is characterized by a slow enough thermal relaxation to consider its study in vivo. Although the activation of the compound GdFAzo is relatively low under the experimental conditions used in vitro (compared to the compound GdAzo, FIG. 1c), it is difficult to predict the molecular activation efficiency that the compound would have in vivo.
(iii) the type of metal to be used to enable activation of the organic unit. It has been shown that the atomic number Z of the metal must be greater than 39 (that of Yttrium) to allow for consistent activation (>30% under 5 Gy). Indeed, 6 compounds containing a metal of size greater than or equal to that of Yttrium showed such activation while 2 compounds containing smaller metals (Cu, Z=29, and Ga, Z=31) showed low activation (<10% under 5 Gy) (FIG. 1f).
(iv) that molecular activation can be performed under various types of ionizing radiation (X-rays, gamma rays, electrons), with different particles (photons and electrons) and different energies (from 1 keV to 4.5 MeV) (FIG. 1c), and thus that the set of radiotherapy devices currently in clinical use should be effective at generating the described molecular activation.
(v) that the compound GdAzo is able to induce the permeabilization of cancer cell membranes under ionizing radiation at low doses (6.9% (vs. 1.2% without irradiation), 8.2% (vs. 2.8% without irradiation) and 12.4% (vs. 7.5% without irradiation) at GdAzo concentrations of 250 μM, 500 μM and 850 μM respectively by gamma rays at 2 Gy) (FIG. 2a,b,c).
(vi) that the compound GdAzo is able to induce toxicity in a gemcitabine-resistant cancer cell line (human acute lymphoblastic leukemia), in the absence or presence of gemcitabine (FIG. 2d,e), after treatment with gamma radiation at 2 Gy In the absence of gemcitabine, cell viability 4 days after treatment was reduced to 23% (vs. 79% without irradiation), 18% (vs. 42% without irradiation) and 3.0% (vs. 27% without irradiation) at GdAzo concentrations of 250 μM, 500 μM and 850 μM respectively. In the presence of gemcitabine, cell viability 4 days after treatment was reduced to 15% (vs. 49% without irradiation), 9.1% (vs. 30% without irradiation) and 1.2% (vs. 16% without irradiation) at GdAzo concentrations of 250 μM, 500 μM and 850 μM respectively. This study shows that the compound is active alone under ionizing radiation and that the presence of a surrounding active substance only slightly enhances the therapeutic effect of the compound (FIG. 2d,e).
(vii) that the presence of the azobenzene or stillbene motif on the molecule is necessary to generate the therapeutic effect since the commercial control compound Dotarem® (gadolinium chelate alone) has no therapeutic effect under ionizing radiation (FIG. 2f).

The invention claimed is:
1. A compound having the formula (IA):

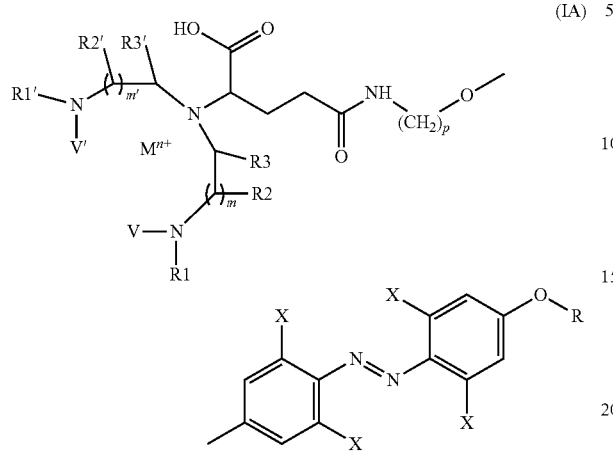

in which:
M represents a metal atom selected from Ce(III), Pr(III), Nd(III), Sm(III), Eu(III), Gd(III), Tb(III), Dy(III), Ho(III), Er(III), Tm(III), Yb(III), Mg(II), Ca(II), Mn(II), Fe(II), Fe(III), Cu(II), Zn(II), Ga(III), Y(III), Zr(III), Tc(IV), Tc(VI), Tc(VII), Ru(II), Ru(III), Ru(IV), Pd(II), Ag(I), In(III), Hf(IV), Re(VI), W(II), W(III), W(IV), W(V), W(VI), Os(III), Os(IV), Ir(III), Ir(IV), Pt(II), Au(I), Au(III), Tl(III), Zr(IV), Nb(III), Bi(III);

n is 1, 2, 3, 4, 5, 6, or 7;

V and V', which may be identical or different, are hydrogen atoms or linear or branched C1-C10 alkyl or alkoxy chains, or C1-C10 alkyl chains linked together and comprising one or more heteroatoms selected from N, O, or S, optionally substituted with one or more substituents independently selected from halogen atoms, and nitrile, nitro, thio, amino, amido, aryl, heteroaryl, hydroxyl, carboxylic acid or carboxylate groups, to form a ring;

R1, R1', R2, R2', which may be identical or different, are hydrogen atoms, or linear or branched C1-C10 alkyl or alkoxy chains optionally substituted with one or more substituents independently selected from halogen atoms, and nitrile, nitro, thio, amino, amido, aryl, heteroaryl, hydroxyl, carboxylic acid or carboxylate groups;

R3 and R3', which may be identical or different, are hydrogen atoms or linear or branched C1-C10 alkyl or alkoxy chains optionally substituted with one or more substituents independently selected from halogen atoms, and nitrile, nitro, thio, amino, amido, aryl, heteroaryl, hydroxyl, carboxylic acid or carboxylate groups, or R3 and R3' are linked together to form a 5- to 14-membered heterocycle or heteroaryl;

m and m', which may be identical or different, are equal to 1 or 2;

p is an integer between 0 and 6;

X is selected from hydrogen and halogen atoms;

R is a linear or branched C1-C12 alkyl group;

the N=N double bond is in cis or trans form;

wherein the n cationic charges of M are optionally neutralized by 0 to n carboxylate groups (—COOH) substituted on R1, R1', R2, R2', R3, R3', V, V', and/or by 0 to n of the counterions present in solution, and cis and/or trans isomers and mixtures thereof.

2. A compound having the general formula (IB):

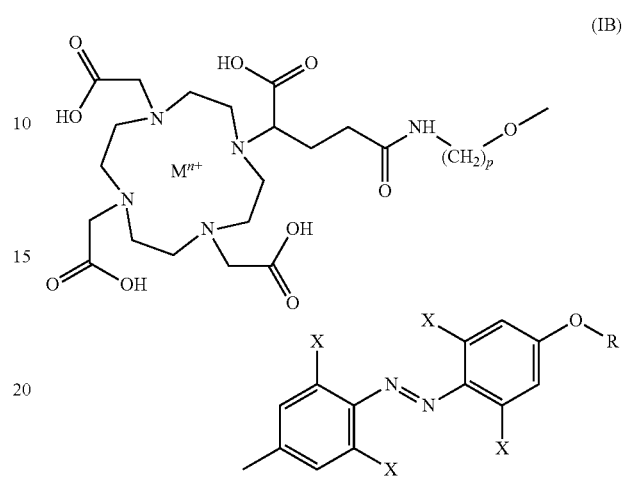

in which

M represents a metal atom selected from Ce(III), Pr(III), Nd(III), Sm(III), Eu(III), Gd(III), Tb(III), Dy(III), Ho(III), Er(III), Tm(III), Yb(III), Mg(II), Ca(II), Mn(II), Fe(II), Fe(III), Cu(II), Zn(II), Ga(III), Y(III), Zr(III), Tc(IV), Tc(VI), Tc(VII), Ru(II), Ru(III), Ru(IV), Pd(II), Ag(I), In(III), Hf(IV), Re(VI), W(II), W(III), W(IV), W(V), W(VI), Os(III), Os(IV), Ir(III), Ir(IV), Pt(II), Au(I), Au(III), Tl(III), Zr(IV), Nb(III), Bi(II);

n is 1, 2, 3, 4, 5, 6, or 7;

p is an integer between 0 and 6;

X is selected from H; halogen atoms; alkoxy, alkyl or cycloalkyl groups optionally interrupted or substituted with one or more heteroatom(s) or group(s) COOH, CONH$_2$, COSH, OH, NH$_2$, SH; 5- to 12-membered aryl or heteroaryl groups optionally substituted with one or more COOH, CONH$_2$, COSH groups; COOH or NH$_2$ groups; and R represents H, or linear or branched C1-C18 alkyl or alkoxy chain, optionally substituted with one or more substituents independently selected from halogen atoms, and nitrile, nitro, thio, amino, amido, aryl, heteroaryl, hydroxyl, carboxylic acid or carboxylate groups.

3. A compound having the general formula (IC):

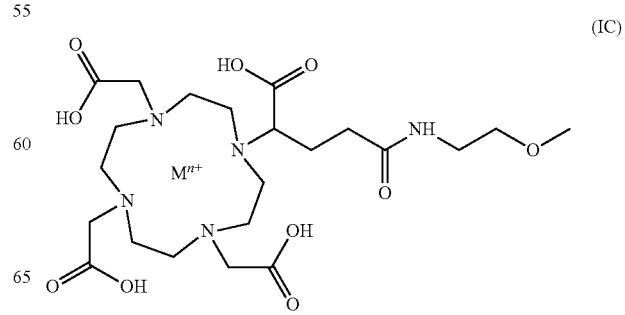

-continued

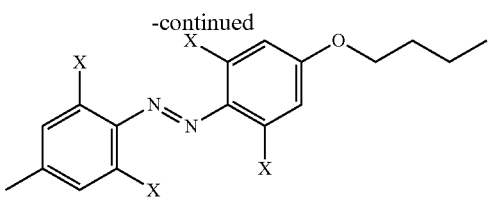

in which

M represents a metal atom selected from Ce(III), Pr(III), Nd(III), Sm(III), Eu(III), Gd(III), Tb(III), Dy(III), Ho(III), Er(III), Tm(III), Yb(III), Mg(II), Ca(II), Mn(II), Fe(II), Fe(III), Cu(II), Zn(II), Ga(III), Y(III), Zr(III), Tc(IV), Tc(VI), Tc(VII), Ru(II), Ru(III), Ru(IV), Pd(II), Ag(I), In(III), Hf(IV), Re(VI), W(II), W(III), W(IV), W(V), W(VI), Os(III), Os(IV), Ir(III), Ir(IV), Pt(II), Au(I), Au(III), Tl(III), Zr(IV), Nb(III), Bi(III);

n is 1, 2, 3, 4, 5, 6, or 7;

X may be selected from H; halogen atoms; alkoxy, alkyl or cycloalkyl groups optionally interrupted or substituted with one or more heteroatom(s) or group(s) COOH, CONH$_2$, COSH, OH, NH$_2$, SH; 5- to 12-membered aryl or heteroaryl groups optionally substituted with one or more COOH, CONH$_2$, COSH groups; COOH or NH$_2$ groups;

and cis and/or trans isomers and mixtures thereof.

4. A method of treating cancer in a subject in need thereof, comprising administering to the subject a therapeutically effective amount of a compound of formula (I):

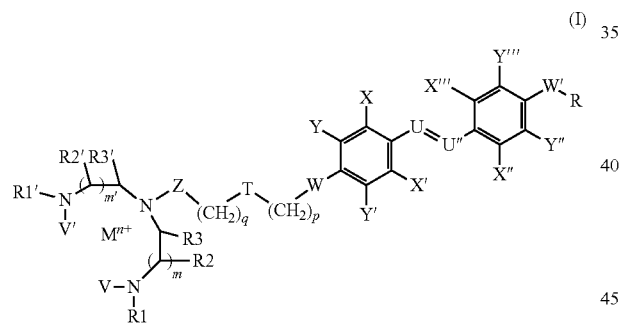

(I)

in which:

M represents a metal atom selected from Ce(III), Pr(III), Nd(III), Sm(III), Eu(III), Gd(III), Tb(III), Dy(III), Ho(III), Er(III), Tm(III), Yb(III), MO(II), Ca(II), Mn(II), Fe(II), Fe(III), Cu(II), Zn(II), Ga(III), Y(III), Zr(III), Tc(IV), Tc(VI), Tc(VII), Ru(II), Ru(III), Ru(IV), Pd(II), Ag(I), In(III), Hf(IV), Re(VI), W(II), W(III), W(IV), W(V), W(VI), Os(III), Os(IV), Ir(III), Ir(IV), Pt(II), Au(I), Au(III), Tl(III), Zr(IV), Nb(III), Bi(III);

n is 1,2,3,4,5,6, or 7;

V and V', which may be identical or different, are hydrogen atoms or linear or branched C1-C10 alkyl or alkoxy chains, or C1-C10 alkyl chains linked together and comprising one or more heteroatoms selected from N, O, or S, optionally substituted with one or more substituents independently selected from halogen atoms, and nitrile, nitro, thio, amino, amido, aryl, heteroaryl, hydroxyl, carboxylic acid or carboxylate groups, to form a ring;

R1, R1', R2, R2', which may be identical or different, are hydrogen atoms, or linear or branched C1-C10 alkyl or alkoxy chains optionally substituted with one or more substituents independently selected from halogen atoms, and nitrile, nitro, thio, amino, amido, aryl, heteroaryl, hydroxyl, carboxylic acid or carboxylate groups;

R3 and R3', which may be identical or different, are hydrogen atoms or linear or branched C1-C10 alkyl or alkoxy chains optionally substituted with one or more substituents independently selected from halogen atoms, and nitrile, nitro, thio, amino, amido, aryl, heteroaryl, hydroxyl, carboxylic acid or carboxylate groups, or R3 and R3' are linked together to form a 5- to 14-membered heterocycle or heteroaryl;

m and m', which may be identical or different, are equal to 1 or 2;

X, X', X", X''', Y, Y', Y", Y''', which may be identical or different, are independently selected from H; halogen atoms; alkoxy, alkyl or cycloalkyl groups optionally interrupted or substituted with one or more heteroatom(s) or group(s) COOH, CONH$_2$, COSH, OH, NH$_2$, SH: 5- to 12-membered aryl or heteroaryl groups optionally substituted with one or more COOH, CONH$_2$, COSH groups; COOH or NH$_2$ groups;

Z represents an alkyl group optionally interrupted or substituted with one or more heteroatom(s) or a COOH, CONH$_2$, COSH, OH, NH$_2$, SH group; a 5- to 12-membered aryl or heteroaryl group optionally substituted with one or more COOH, CONH$_2$, COSH groups; or a COOH or NH$_2$ group;

W and W', which may be the same or different, independently represent a CH$_2$ group; or an aryl or cycloalkyl group; an oxygen or nitrogen atom (secondary or ternary); an amide linkage; an ester linkage; a thioether linkage;

U and U', which may be the same or different, represent the CH or NH group, it being understood that the double bond U=U' is in cis or trans form;

T represents a CH$_2$ group; a —C(=O)NH group; an alkoxy, alkyl or cycloalkyl group optionally interrupted or substituted with one or more heteroatom(s) or a COOH, CONH$_2$, COSH, OH, NH$_2$, SH group; a 5- to 12-membered aryl or heteroaryl group containing one or more heteroatom(s) and/or optionally substituted with one or more groups chosen from COOalkyl, CONHalkyl, COSHalkyl;

R represents H, or linear or branched C1-C18 alkyl or alkoxy chain, optionally substituted with one or more substituents independently selected from halogen atoms, and nitrile, nitro, thio, amino, amido, aryl, heteroaryl, hydroxyl, carboxylic acid or carboxylate groups;

p and q are integers between 0 and 6;

wherein the n cationic charges of M are optionally neutralized by 0 to n carboxylate groups (—COOH) optionally substituted on R1, R1', R2, R2', R3, R3', V, V', and/or by 0 to n of the counterions present in solution;

and cis and/or trans isomers and mixtures thereof, wherein the cancer is selected from the group consisting of lung cancer, pancreatic cancer, liver cancer, spleen cancer, small cell lung carcinoma, prostate cancer, rhabdomyosarcoma, stomach cancer, gastrointestinal cancer, colorectal cancer, kidney cancer, breast cancer, ovarian cancer, testicular cancer, thyroid cancer, head and neck cancer, skin cancer, soft tissue sarcoma, bladder carcinoma, bone cancers, myeloma, plasmacytoma, germ cell cancer, uterine cancer, leukemia, lymphoma, neuroblastoma, osteosarcoma, retinoblastoma, central nervous system cancers, and Wilms' tumors.

5. The method according to claim 4, wherein the compound (I) is predominantly in cis form, and further comprising a step of irradiating a tumor caused by the cancer with ionizing radiation.

6. The method of claim 4, further comprising monitoring said treatment by in vivo medical imaging.

7. The method of claim 4, further comprising administering one or more chemotherapy and/or immunotherapy anti-cancer agents to the subject.

8. The method of claim 5, wherein the ionizing radiation is X-rays, gamma rays, electron beams or hadron beams.

9. The method of claim 8, wherein the hadron beams comprise protons and/or carbon ions.

10. The method of claim 6, wherein the in vivo medical imaging is MRI, PET, X-ray or SPECT.

11. The method of claim 7, wherein the one or more chemotherapy and/or immunotherapy anti-cancer agents include at least one immune checkpoint inhibitor.

12. The method of claim 11, wherein the at least one immune checkpoint inhibitor is anti-CTLA4, anti-PD-L1 or anti-PD1.

* * * * *